(12) United States Patent
Kashanin et al.

(10) Patent No.: US 8,802,391 B2
(45) Date of Patent: Aug. 12, 2014

(54) METHOD FOR MEASURING THE MIGRATION OF CELLS IN A CHANNEL UNDER THE INFLUENCE OF AN ANALYTE

(71) Applicant: Cellix Limited, Dublin (IE)

(72) Inventors: Dmitry Kashanin, Dublin (IE); Igor Shvets, Dublin (IE); Vivienne Williams, Dublin (IE); Frank O'Dowd, Ballybunion (IE)

(73) Assignee: Cellix Limited, Dublin (IE)

( * ) Notice: Subject to any disclaimer, the term of this patent is extended or adjusted under 35 U.S.C. 154(b) by 0 days.

(21) Appl. No.: 13/648,677

(22) Filed: Oct. 10, 2012

(65) Prior Publication Data
US 2013/0040334 A1 Feb. 14, 2013

Related U.S. Application Data

(63) Continuation of application No. 12/407,902, filed on Mar. 20, 2009, now abandoned.

(51) Int. Cl.
*C12Q 1/24* (2006.01)

(52) U.S. Cl.
USPC ........ 435/30; 435/297.5; 435/308.1; 210/296

(58) Field of Classification Search
USPC ....................... 435/30, 297.5, 308.1; 210/296
See application file for complete search history.

(56) References Cited

U.S. PATENT DOCUMENTS

| | | |
|---|---|---|
| 6,770,434 B2 | 8/2004 | Shvets et al. |
| 7,122,301 B2 | 10/2006 | Shvets et al. |

FOREIGN PATENT DOCUMENTS

| | | |
|---|---|---|
| EP | 1 221 617 A2 | 7/2002 |
| WO | WO 2006/025858 A2 | 3/2006 |

OTHER PUBLICATIONS

Chueh et al., Leakage-free bonding of porous membranes into layered microfluidic array systems, Analytical Chemistry, American Chemical Society, vol. 79, No. 9, May 1, 2007, pp. 3504-3508, XP002581711.

Kimura et al., An integrated microfluidic system for long-term perfusion culture and on-line monitoring of intestinal tissue models, Lab on a Chip, vol. 8, No. 5, 2008, pp. 741-746, XP002581710.

Wong et al., Partitioning microfluidic channels with hydrogel to construct tunable 3-D cellular microenvironments, Biomaterials, Elsevier Science Publishers BV., Barking, GB vol. 29, No. 12, Feb. 19, 2008, pp. 1853-1861, XP022499083, ISSN: 0142-9612.

European Search Report dated May 10, 2010 for Application No. EP10157105.

*Primary Examiner* — Ralph Gitomer
(74) *Attorney, Agent, or Firm* — Choate, Hall & Stewart LLP; Andrea L. C. Robidoux

(57) ABSTRACT

The present invention is directed to a method for measuring the migration of cells in a channel under the influence of an analyte wherein said cells are separated from said analyte by a semi-permeable membrane and said cells are subjected to controlled flow conditions while the analyte is static and in the form of a viscous substance or gel.

18 Claims, 15 Drawing Sheets

METHOD FOR MEASURING THE MIGRATION OF CELLS IN A CHANNEL UNDER THE INFLUENCE OF AN ANALYTE

RELATED APPLICATIONS

This application is a continuation of U.S. patent application Ser. No. 12/407,902, filed Mar. 20, 2009 now abandoned; the entirety of which is incorporated herein by reference.

FIELD OF THE INVENTION

The present invention is directed to a biochip assembly comprising a semi-permeable membrane and a method using said biochip assembly for carrying out cell based assays.

BACKGROUND OF THE INVENTION

The ability to monitor migration of biological cells through tight layer of other cells and tissues is crucial for understanding of mechanism of many life threatening diseases and development of modern therapeutic drugs. This migration is typically triggered by the presence of a particular chemical either immobilized on a surface or diffused through a tissue.

In inflammatory conditions, for example, the migration of leukocytes from blood vessels into diseased tissues is crucial to the initiation of normal disease-fighting inflammatory responses. At the same time, this process, known as leukocyte recruitment, is also involved in the onset and progression of debilitating and life-threatening inflammatory and autoimmune diseases. Thus, the ability to control the migration of leukocyte through blood vessels into healthy tissues is an important pathway for development of therapeutic treatment. This migration is complicated by the fact that several leukocyte classes participate in this pathology (including lymphocytes, monocytes, neutrophils, eosinophils and mast cells) and each class carries out its own physiological function. There is the whole range of chronic autoimmune diseases. These include psoriasis, atherosclerosis, rheumatoid arthritis, contact dermatitis, multiple sclerosis, inflammatory bowel disease, hepatitis, sarcoidosis, idiopathic pulmonary fibrosis, dermatomyositis and diabetes. There are also numerous organ transplant rejection conditions such as allograft rejection and graft-versus-host disease that are determined to a large extent by the leukocyte migration.

The process by which leukocytes leave the bloodstream and accumulate at inflammatory sites and initiate the disease takes place in three distinct steps (Lawrence and Springer, 1991, Cell 65:859-73; Butcher E. C. 1991, Cell 67: 1033-36; Springer, T. A. 1990, Nature, 346: 425-33;). It is mediated by chemoattractant receptors, by cell-surface proteins, called adhesion molecules, and by the ligands that bind to these two classes of cell-surface receptors. The major types of adhesion molecules are known as "selectins", "integrins" and "immunoglobulin (Ig) family" receptors.

Each of the three steps is essential for the migration of the leukocytes to target tissues. Blocking these steps has been shown to prevent a normal inflammatory response, and promotes abnormal responses of inflammatory and autoimmune diseases (Harlan et al., 1992, In vivo models of leukocyte adherence to endothelium. In Adhesion: Its Role in Inflammatory Disease., J. M. Harlan and D. Y. Liu, (eds.), W. H. Freeman & Co., pp. 117-150).

The three steps of leukocyte adhesion and transendothelial migration can be summarized as follows:

Step 1—Primary adhesion. Leukocytes attach loosely to the blood vessel endothelium and "roll" slowly along the blood vessel wall, pushed by the flow of blood. Leukocyte-endothelium attachment is mediated by cell surface adhesion molecules called "selectins" which bind to carbohydrate-rich ligands ("glycoconjugates") on the leukocyte cell surface.

Step 2—Activation of leukocytes and migration to the target site. Chemoattractant receptors on the surface of the leukocytes bind chemoattractants secreted by cells at the site of damage or infection. Receptor binding activates the immune defenses of the leukocytes, and activates the adhesiveness of the adhesion molecules that mediate Step 3.

Step 3—Attachment and transendothelial migration. The leukocytes bind very tightly to the endothelial wall of the blood vessel and move to the junction between endothelial cells, where they begin to squeeze between these cells to reach the target tissue. This tighter binding is mediated by binding to adhesion receptors called "integrins" on the leukocytes to complementary receptors of the "Ig family" on the endothelium. (The Ig family molecules are named for their similarity to antibody molecules (immunoglobulins)). Chemoattractant receptors are also involved at this stage, as the leukocytes migrate up a concentration gradient of the chemoattractant secreted by cells at the target site.

It is increasingly clear that there may be another step preceding primary adhesion, i.e. preceding step 1, called "margination". As a result of margination leukocytes get pushed by the red blood cells to the periphery of blood vessel, thereby allowing leukocytes to interact with the endothelium. However, margination is not commonly accepted as yet in the three step migration process described above.

These three steps of receptor-ligand interactions are all required and appear to act in a highly cooperative and coordinated manner to mediate leukocyte adherence to the microvasculature, diapedesis, and subsequent leukocyte mediated injury to tissue in inflammatory disease.

LFA-1 and Mac-1 together comprise the leukocyte integrins, a subfamily of integrins that share a common beta subunit (CD18) and have distinct alphaL, alpha M and alpha.X (CD11a, b and c) alpha subunits (Springer, 1990, Nature 346:425-433). They are required for leukocyte emigration as demonstrated by an absence of neutrophil extravasation (1) in patients with mutations in the common beta subunit (leukocyte adhesion deficiency), and (2) after treatment of healthy neutrophils with a monoclonal antibody (mAb) to the common beta subunit in vivo or in vitro.

The integrins LFA (lymphocyte function-associated antigen)-1 and Mac-1 on the neutrophil bind to the Ig family member ICAM (intercellular adhesion molecule)-1 on endothelium (Diamond et al., 1990, J. Cell Biol. 111:3129-3139). LFA-1 binds to ICAM-2, an endothelial cell molecule that is more closely related to ICAM-1 than these molecules are to other Ig superfamily members (Staunton et al., 1989, Nature 339:61-64).

The integrin VLA-4, that contains the alpha.4 (CD49d) subunit noncovalently associated with the beta1 (CD29) subunit, is expressed by lymphocytes, monocytes, and neural crest-derived cells, and can interact with vascular cell adhesion molecule-1 (VCAM-1) (Elices et al., 1990, Cell 60:577). Like ICAM-1 and ICAM-2, VCAM-1 is a member of the Ig superfamily (Osborn et al., 1989, Cell 59:1203).

Chemoattractants are soluble mediators which activate cell adhesion and motility and direct cell migration through formation of a chemical gradient. They are produced by bacteria and numerous cell types including stimulated endothelial and stromal cells, platelets, tumor cells, cultured cell lines, and leukocytes themselves. The cells responding to chemoattractants appear to express specific receptors on their surfaces which bind the chemoattractant molecules and sense the gradient. Receptor stimulation induces cells to respond via a common signal transduction pathway which involves interaction of the chemoattractant-receptor complex with a guanine nucleotide or GTP-binding protein (G protein). This interaction stimulates phosphatidyl inositol hydrolysis by a phospholipase C, thus generating inositol phosphates and diacylglycerol. A transient rise in cytosolic free calcium then activates protein kinase C, and a variety of events including protein phosphorylation, membrane potential changes, and intracellular pH alterations ensue.

Several of the chemoattractants primarily affecting neutrophils were among the first chemoattractants identified. These include the complement component C5a, arachidonate derivative leukotriene $B_4$ ($LTB_4$), platelet activating factor (PAF), and formylmethionyl peptides of bacterial origin such as formyl-met-leu-phe (fMLP). Although structurally dissimilar and stimulatory via separate receptors, these molecules produce a rapid and marked increase in neutrophil adhesiveness and motility leading to chemotaxis and prominent neutrophil accumulation in vivo. The receptors for C5a and fMLP have been identified and sequenced; cDNA clones for each have also been generated (Gerard and Gerard, 1991, Nature 349:614-617). These receptors share many structural features with one another and members of the "rhodopsin superfamily" of protein receptors.

The chemoattractants which predominantly activate and guide monocytes include monocyte chemoattractant protein-1 (MCP-1) (Leonard and Yoshimura, 1990, Immunol. Today 11:97-101), the RANTES protein (Schall et al., 1990, Nature 347:669-71), and the neutrophil .alpha. granule protein CAP37, among others. MCP-1 and RANTES are structurally homologous and belong to the subfamily of chemoattractive cytokines that are defined by a configuration of four cysteine residues in which the first two are adjacent (C—C). CAP37's structure is most homologous to proteins of the serine protease family (Peteira et al., 1990, J. Clin. Invest. 85:1468-76).

Compared with neutrophil and monocyte chemoattractants, little is known about chemoattractants for lymphocytes. The best characterized lymphocyte chemoattractants are RANTES and IL-8, which primarily attract monocytes and neutrophils. Several in vitro studies have described lymphocyte chemotactic activities in the culture supernatants of mixed lymphocyte reactions and mitogen-stimulated human peripheral blood mononuclear cells (Center and Cruikshank, 1982, J. Immunol. 128:2563-68; Van Epps et al., 1983, J. Immunol. 131:687).

Although considerable effort has been invested on the study of lymphocyte chemoattractants, they remain poorly characterized relative to monocyte and neutrophil chemoattractants. Chemoattractants for the latter cell types, such as MCP-1 and IL-8, have been purified based on the conventional chemotaxis assay, sequenced, and cloned. However, no molecule identified primarily as a lymphocyte chemoattractive factor has been sequenced and cloned.

The devices for studies and monitoring of transmigration of cells are well known in the fields of cell biology, life science, medicine, pharmaceutical and the area of drug development. There are also devices for filtering, growth and grouping of cells in these fields.

The most widely used assay is the Boyden Chamber assay, in which a microporous membrane divides two chambers, the lower containing the test chemoattractant and the upper containing the cells, e.g. lymphocytes. The microporous membrane is commonly nitrocellulose or polycarbonate, and may be coated with a protein such as collagen. The distance of migration into the filter, the number of cells crossing the filter that remain adherent to the undersurface, or the number of cells that accumulate in the lower chamber may be counted.

Such a Boyden chamber is also known as a transwell chamber. The chamber is made of well divided into two compartments, the upper and lower chamber, by a filter containing pores. A chemoattractant or other solution is placed in the lower chamber and the suspension cell is placed in the upper chamber. Cells can then migrate through the pores, across the thickness of the filter, and toward the source of chemoattractant. Cells that migrated across the filter and attached to the underside are then counted. In some assays the membrane is coated with Extra-Cellular Matrix (ECM) proteins (e.g. laminin, collagen, fibronectin) and then with endothelial cells (EC). A variety of devices of this class as well as the method for the transendothelial assay are described in U.S. Pat. No. 5,514,555 (Springer).

Boyden chambers are commonly used for studies of disease and also for the development of drugs for disease treatment. Here we list some examples of these applications:

Prostate cancer: It is not fully understood at present time the mechanism of the bone metastasis. However, interaction between cancer cells and bone environment (extra cellular matrix: ECM) seems critical for the process [Chen, N., et al., A Secreted Isoform of ErbB3 Promotes Osteonectin Expression in Bone and Enhances the Invasiveness of Prostate Cancer Cells. Cancer Res, 2007. 67(14): p. 6544-8]. The ability of prostate cancer cells to penetrate a synthetic basement membrane was assessed in a Matrigel-Boyden chamber invasion assay (BD Biosciences).

Allergy inflammation: the typical study is based on the eosinophils migration. Assay performed in a 48-well microchamber (neuroprobe) [Wong, C. K., P. F. Cheung, and C. W. Lam, Leptin-mediated cytokine release and migration of eosinophils: Implications for immunopathophysiology of allergic inflammation. Eur J Immunol, 2007].

Migration of vascular smooth muscle cells: key step in diseased arteries and may be controlled by ECM [Koyama, N., et al., Heparan sulfate proteoglycans mediate a potent inhibitory signal for migration of vascular smooth muscle cells. Circ Res. 1998. 83(3): p. 305-13].

Chemotactic ability of dental plaque: Whole plaque suspensions were chemotactic for polymorphonuclear leukocytes [Miller, R. L., L. E. Folke, and C. R. Umana, Chemotactic ability of dental plaque upon autologous or heterologous human polymorphonuclear leukocytes. J Periodontol, 1975. 46(7): p. 409-14].

Boyden chambers/Transwell chamber and closely related devices are available from a number of vendors such as BD Biosciences; Corning; Neuroprobe; Millipore. Despite this, Boyden Chamber assays are typically associated with certain shortcomings. These include:

Intravital microscopy studies have suggested that leukocytes transmigration occurs over a time frame of minutes. In contrast, the readouts of most Boyden chamber transfilter assays are taken 1-4 hours after cell introduction. This excessive time span is necessary in order to get reasonable statistics of cell migration.

No physiological flow can be established in this assay thus is not possible to monitor cells though all stages of leukocyte recruitment.

There is no control of the gradient: chemokine diffusion in the body might be different than in vitro as it takes longer to get a cell migration on in vitro assays.

Changes in cell morphology during chemotaxis cannot be observed in real-time (because cells transmigrate through the filter).

In addition, Boyden chamber assays cannot readily answer many questions related to the leukocyte migration. This is particularly true for the molecular and cellular mechanism of the chemokine-induced transendothelial migration step of leukocytes that still have not been fully elucidated. It is not clear at all if positive, negative or any chemokine gradients are involved and how such gradients may physically persist in relation to the endothelium. Initially it was thought that chemokines form soluble gradients across the blood vessel Endothelial Cells (ECs). However, in blood even a short persistence of a soluble chemokine gradient is not feasible because the constant flow of plasma removes the soluble chemokines from the site of their production. Therefore, it has been suggested already over a decade ago that only those chemokines that have been physically retained (immobilized) on the luminal membrane, for example by the glycosaminoglycan (GAG) residues of glycoproteins, may be able to effectively induce the integrin activation of the rolling leukocytes [Rot, A., *Contribution of Duffy antigen to chemokine function*. Cytokine Growth Factor Rev, 2005. 16(6): p. 687-94]. It is known though that a gradient of chemokine can direct cells and it is also well established that ECs protein receptors are necessary for cell adhesion.

There are other known assay types of assays for studies of cell migration. For example, the Dunn chamber assay comprises concentric rings separated by a bridge. The inner ring is filled with medium and the outer ring is filled with chemoattractant solution. Cells are cultured on a coverslip and placed upside down onto the Dunn chamber. The assays allow observation of migrating of cells towards the gradient formed between both rings.

Another area of applications that is broadly related to the area of transmigration is the growth of mammalian cells. A number of methods for culturing mammalian cells of different tissue origins have been reported. However, many of these cells are difficult to grow in vitro and, when grown, are not morphologically similar to in vivo tissue. It would be desirable to produce a tissue and cells which are morphologically similar to their in vivo counterpart for in vitro toxicology and other studies (for example, transepidermal drug transport).

Similarly there are requirements for tests of cells under continuous flow conditions resulting from the area of toxicity. Once identified, candidate drugs or modulators are usually evaluated for bioavailability and toxicological effects (Lu, Basic Toxicology, Fundamentals, Target Organs, and Risk Assessment, Hemisphere Publishing Corp., Washington (1985); U.S. Pat. No. 5,196,313 to Culbreth and U.S. Pat. No. 5,567,592 to Benet). Traditionally, early stages of drug discovery and development have concentrated on optimizing binding and potency of experimental compounds. Typically, animal studies are performed on late stage pre-clinical drug candidates to characterize pharmacokinetics (PK), pharmacodynamics (PD) and physiological toxicity. However, animal studies are costly, time-consuming and are limited, by throughput, to characterize no more than a few compounds. Furthermore, several drugs have shown unanticipated or unpredicted side effects only after reaching clinical trials or wide-scale release to the public. The pharmaceutical industry has the ultimate goal of replacing animal studies with in vitro tests that are validated, predictive models for human toxicity and drug dynamics. More recently, the industry has set a medium-term goal of creating high-throughput, in vitro tests that annotate candidate compounds with adsorption, metabolism and toxic (hereinafter referred to as "ADMET") predictive parameters.

The toxicology of a candidate modulator can be established by determining in vitro toxicity towards a cell line, such as a mammalian, including human, cell lines. Candidate modulators can be treated with, for example, tissue extracts, such as preparations of liver (such as microsomal preparations) to determine increased or decreased toxicological properties of the chemical after being metabolized by a whole organism. The results of these types of studies are often predictive of toxicological properties of chemicals in animals, such as mammals, including humans. Current methods designed to model drug absorption in vivo involve growing a confluent layer of cells on a porous matrix that allows the test compound to permeate through the cell layer and matrix to a bottom well. It is desirable to carry out many of these measurements under conditions of continuous flow. These would mimic better the real physiological conditions. The complexity and interplay of biological processes that must be simulated to predict the ADMET properties of a compound far exceed the capabilities of currently available methods and tools. For example, when a patient takes a drug, it must first pass through the gastrointestinal tract and penetrate into the bloodstream. The drug must then survive oxidative modifications in the liver and get to the desired site (e.g., target organ or primary tumor) in a sufficient therapeutic concentration. Even if these biological functions could be faithfully reproduced in vitro, a difficulty remains in getting the capacity and format of the assay to facilitate testing and analysis of thousands of compounds. Ideally, the assays should be versatile enough to not only measure the enzyme cascade activity inside any living or whole cell, no matter what its origin might be, including cancer cells, tumor cells, immune cells, brain cells, cells of the endocrine system, cells or cell lines from different organ systems, biopsy samples etc., but should also be able to detect and measure the permeability of the cell to the candidate compound, as well as the metabolic activity of the cell on the candidate drug compound. Methodologies are desired that will allow for the more rapid acquisition of information about drug candidate interactions with enzymes that may potentially metabolize the candidate drug, earlier in the drug discovery process than presently feasible. This will allow for the earlier elimination of unsuitable compounds and chemical series from further development efforts, and also give an investigator insight as to the nature of metabolites with potential biological activity derived from the candidate drug. A parallel flow chamber may be used for this purpose. However, there are several disadvantages when using the parallel chamber. For example, the parallel flow chamber requires a substantial amount of the drug candidate for the experiment. Furthermore, setting up the experiment is often time consuming and rather complex.

By way of example, liver hepatocytes express a family of enzymes called cytochromes. One subfamily of cytochromes is known as cytochrome P450. The cytochrome P450 enzyme (CYP450) family comprises oxidase enzymes involved in the xenobiotic metabolism of hydrophobic drugs, carcinogens, and other potentially toxic compounds and metabolites circulating in blood. Efficient metabolism of a candidate drug by a CYP450 enzyme may lead to poor pharmacokinetic properties, while drug candidates that act as potent inhibitors of a CYP450 enzyme can cause undesirable drug-drug interactions when administered with another drug that interacts with the same CYP450. See, e.g., Peck, C. C. et al, Understanding Consequences of Concurrent Therapies, 269 JAMA 1550-52 (1993). Accordingly, early, reliable indication that a candidate drug interacts with (i.e., is absorbed by, metabolized by, or toxic to) hepatocytes expressing CYP450 may greatly shorten the discovery cycle of pharmaceutical research and development, and thus may reduce the time required to market a candidate drug. Consequently, such earlier-available, reliable pharmacokinetic information may result in greatly reduced drug development costs and/or increased profits from earlier market entrance. Furthermore, such earlier-available, reliable pharmacokinetic information may allow a candidate drug to reach the public sooner, at lower costs than otherwise feasible. Accordingly, extensive pharmacokinetic studies of drug interactions in humans have recently become an integral part of the pharmaceutical drug development and safety assessment process, e.g., Parkinson, A., 24 Toxicological Pathology 45-57 (1996).

Thus, despite the advances made to date, there remains a need to provide improved systems for carrying out cell based assays.

SUMMARY OF THE INVENTION

The invention provides method and devices for performing cell based assays and cell tests.

According to a first aspect of the invention, there is provided a method for measuring the migration of cells in a channel under the influence of an analyte wherein said cells are separated from said analyte by a semi-permeable membrane and said analyte and/or said cells are subjected to controlled flow conditions. Essentially, the semi-permeable membrane is mounted in the channel and acts as a divider wall defining a sample channel and an analyte channel.

An objective of the invention is to provide a system and method for the study of the migration of the cells under conditions mimicking more closely in-vivo situation than some of the currently available systems and methods.

A further objective is to provide a system and method for the study of transmigration of the cells through a layer of cells under conditions mimicking more closely the in-vivo situation, such as for example the conditions of the continuous flow modeling shear stress on cells, conditions of the pulsating flow modeling conditions of pulsating shear stress.

Another objective is to provide a system and the method for the study of cell-ligand interactions, such as the binding of cells to ligands, and cell to cell interactions such as cell to cell binding and adhesion.

A still further objective of the invention is to provide the system for studies of the cell response or cell function to drug or drug candidates. This response or function may include any of the following by way of example. The test compound may: (1) kill or decrease the viability of the test cell; (2) be metabolized or chemically altered by the test cell; (3) pass through the test cell unchanged, (4) be unreleasably absorbed by the test cell; (5) cause the movement of the test cell through the membrane or substrate surface; or (6) cause the detachment of the test cell from the membrane or substrate surface.

The present invention aims to address at least some of the above objectives.

Ideally, the migration of cells is transmigration and the method of the invention facilitates the transmigration of cells through the semi-permeable membrane.

Ideally, the sample cells and/or analyte are introduced at a controlled steady flow rate across the channel/biochip. In this way cells may be delivered across the semi-permeable membrane wherein analyte is present on the opposed surface thereto.

Ideally, such a channel has a width in the range from approximately 0.005 to 20 mm, more preferably in the range from approximately 0.1 to 10 mm and a depth in the range of from approximately 0.005 to 3 mm, more preferably in the range from 0.05 to 0.5 mm. According to one embodiment, the channel has a width of approximately 100 to 500 microns. It will be understood that the width and the depth of the channel do not need to be constant all across its entire length, and indeed may change considerably between different parts of the channel. The advantage of this is that the assembly may be used to mimic situations where capillaries or other portions of a patients body might be constricted. For examples, blocking if the arteries and the like, may be easily studied. The cross-sectional area or bore of the channel may be cylindrical or non-cylindrical. Optionally, the bore size may be chosen to mimic the bore size of capillaries or venules of a human.

Ideally, the method takes place in an elongate enclosed channel having a semi-permeable membrane mounted therein. It will be understood the channel may be a microchannel, preferably an elongate enclosed microchannel. In this manner, the semi-permeable membrane may act as a divider wall in the elongate enclosed channel, separating the sample channel from the analyte channel. Alternatively, two or more elongate enclosed channels are connected by the semi-permeable membrane, Many different assays (e.g. monitoring cell transmigration in a channel/biochip etc) may be carried out and examples of such assays are expanded on below.

Preferably, said cells are present on at least one side of said semi-permeable membrane and said analyte is present on the opposed surface thereto.

In the method, the sample cells and/or the analyte are ideally introduced into the channel at a controlled steady flow rate. According to one embodiment, said cells or said analyte on one side only of said membrane is subjected to controlled flow. According to an alternative embodiment, said cells or said analyte on both sides of said membrane are subjected to controlled flow.

It will be understood that said analyte may be a reagent liquid or gel. Thus, the analyte may be a chemoattractant, a toxic substance and/or a pharmaceutical preparation. The reagent gel may be in the form of a solid or semi-solid gel. For example, the reagent liquid may comprise ECM gel containing IL-8. It will also be understood that the reagent in certain cases may be a placebo.

According to a preferred embodiment of this aspect of the invention, the method further comprises forming a layer of seeded cells adjacent to at least one side of said semi-permeable membrane. Ideally, said layer of seeded cells is formed on the semi-permeable membrane prior to use and said semi-permeable membrane with seeded cells is mounted in the channel prior to use. The seeded cells may form either a confluent or non-confluent layer adjacent to at least side of said semi-permeable membrane. Such seeded cells may be endothelial cells.

In another embodiment of this aspect of the invention, the method further comprises coating at least one side of the semi-permeable membrane with one or more substances which effect cell function prior to forming a layer of seeded cells on said semi-permeable membrane. Ideally, such substance promotes adhesion of cells. Such substances may be in any form, such as a gel, liquid etc.

The method may also comprise a further step of coating the internal bore of the channel prior to use with a substance which interacts with said seeded and/or sample cells. Such a substance is ideally a cell adhesion molecule and/or a cell transmigration substance. To facilitate the attachment of these substances, the walls of the channel may be treated, e.g. by plasma treatment, so that they become hydrophilic. Alternatively, they may be coated by a hydrophilic coating such as liquid silicon. Such a hydrophobic coating ensures that cells do not adhere to the walls of the channel and detrimentally effect the results.

In one application of the method the interaction between said seeded cells and said sample cells is monitored and/or recorded.

In another application of the method, the physiological function of said seeded cells is monitored and/or recorded.

In yet another application of the method, the physiological function of said seeded cells is measured as a function of the shear stress within the channel.

In a still another application of the method, the method comprises introducing analyte to said channel and monitoring and/or recording the response of said seeded cells and/or sample cells to said analyte, in terms of adsorption, metabolism and/or toxicity.

In another application, the method comprises measuring cell to cell interactions and cell to analyte interactions.

It will be understood that the flow conditions may be sustained by a pressure driven pumping system or a positive displacement pumping system or any other suitable means.

In a preferred embodiment of the invention, the method comprises causing sample cell containing liquid to flow in at least one elongate enclosed channel having a semi-permeable membrane mounted therein, thereby delivering sample cells against the semi-permeable membrane having a reagent liquid on the opposed surface thereto.

According to a second aspect of the invention, there is provided a biochip assembly for carrying out assays with living cells wherein the assembly comprises at least one elongate enclosed channel having a semi-permeable membrane mounted therein.

Ideally, the assay is a transmigration assay and the method involves measuring the transmigration of cells.

According to one embodiment, the assembly comprises a plurality of elongate enclosed channels.

Ideally, the channel is a microchannel, preferably an elongate enclosed microchannel.

Ideally, the semi-permeable membrane acts as a divider wall separating the elongate enclosed channel into a first channel and a second channel. In use, the first channel may receive sample cells and the second channel may receive analyte or vice versa. It will also be understood, that depending on the assay being carried out, both channels may receive both cells and analyte.

According to another embodiment, the biochip assembly for carrying out assays with living cells comprises at least one elongate enclosed channel having a semi-permeable membrane mounted therein wherein the semi-permeable membrane forms a connecting wall between at least two adjoining channels. Ideally, the assembly comprises a first and second channel wherein the first channel receives said sample cells and the second channel receives said analyte.

The channel assembly of the invention may be arranged in several different ways. These type of constructions are described in more detail in relation to the figures.

For example, the adjoining channels may be in line and as such run parallel to each other. Alternatively, the adjoining channels may intersect at one section of the channel only. Additionally, the semi-permeable membrane abuts the elongate enclosed channel.

The semi-permeable membrane may permit unidirectional or bidirectional flow.

In one embodiment, only a defined part or length of the channel is in contact with the said semi-permeable membrane.

In another embodiment, the semi-permeable membrane comprises one or more semi-permeable membrane types characterized by different membrane properties, for example each semi-permeable membrane type has a different pore size and/or different membrane size.

In yet another embodiment, at least one surface of the semi-permeable membrane comprises one or more substances which effect cell function, preferably a substance which promotes the adhesion of cells. The semi-permeable membrane is ideally a microporous membrane.

Ideally, the semi-permeable membrane is a cell transparent membrane. Optionally, the cell transparent membrane may be seeded with cells. The cell transparent membrane may be selectively permeable to different cell types.

It is envisaged that the channel according to the invention will generally have a planar top wall to allow good optical properties for examination under a microscope and generally speaking, the channel comprises planar top, bottom and side walls (i.e. non-cylindrical cross-section).

It is also envisaged that assemblies comprising a plurality of biochips as described above will be formed on one base sheet and will preferably have various common feeder channels having ports therein. This provides for ease of examination under the microscope.

According to another aspect of the invention, there is a biochip assembly for carrying out assays with living cells wherein the assembly comprises at least one elongate enclosed channel and a well wherein a semi-permeable membrane separates said channel from said well. Ideally, the semi-permeable membrane is mounted in the elongate enclosed channel.

BRIEF DESCRIPTION OF THE DRAWINGS

The invention will now be more clearly understood with reference to the following description given by way of example only and the following non-limiting figures. For clarity in viewing the drawings, where possible the same numbering for identical parts has been used in FIGS. 1 to 15.

DETAILED DESCRIPTION OF THE INVENTION

Figure 1:
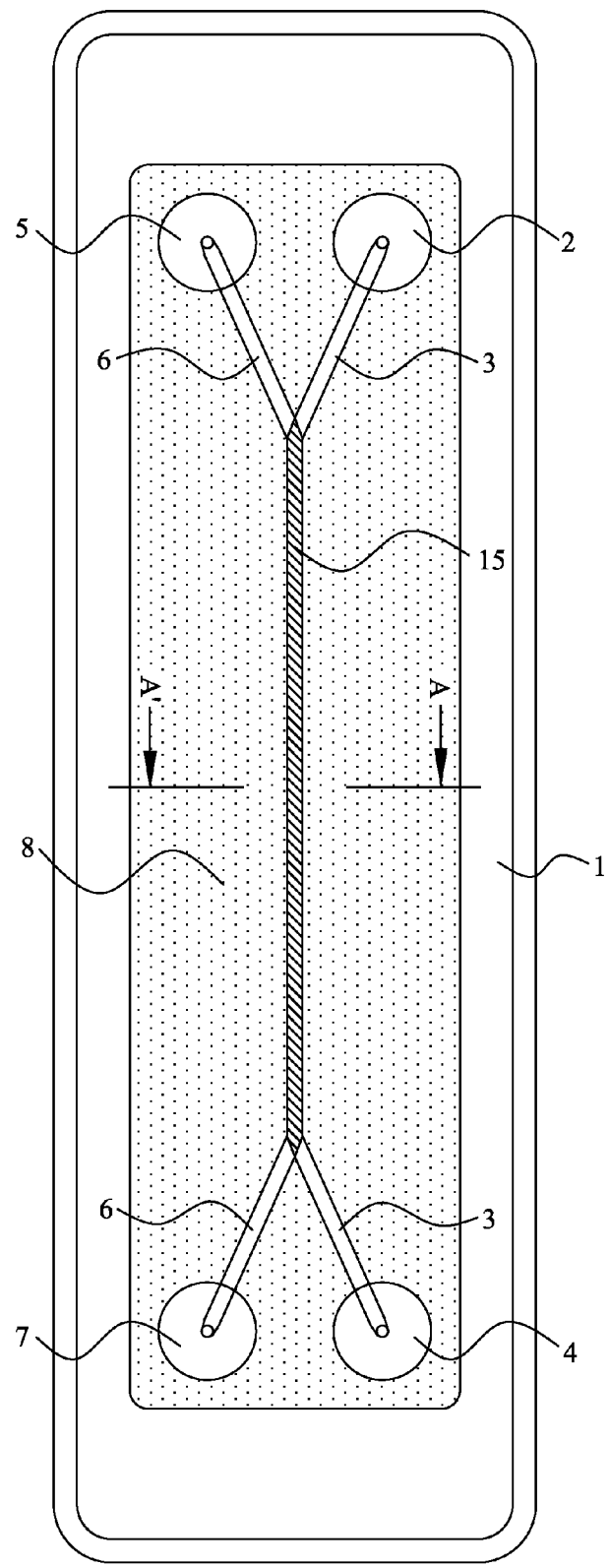
FIG. 1. is a plan view of a transmigration device of the invention showing the sample channel and analyte channel in line.

The invention provides a device and method for performing cell-based assays and cell tests. Prior to discussing this invention and figures in further detail, the following terms used in the specification will first be explained.

The term "cell" includes both eukaryotic and prokaryotic cells, including but not limited to bacteria, yeast, mammalian cells. The use of plant cells may also be contemplated. Preferably the cells are eukaryotic cells. According to one particularly preferred embodiment the cells are leukocytes, such as neutrophils, lymphocytes etc.

The term "sample cells" or "sample cell containing liquid" ideally refers to a suspension of living cells within a suitable carrier medium, for example, a culture medium. Such a culture medium is ideally in liquid form but is not limited to this form. It will be understood that more than one type of cell may be in the suspension.

The semi-permeable membrane may be a cell-transparent membrane. These terms will be used interchangeably in the specification. The term "cell transparent membrane" encompasses a film or membrane that contains holes or pores large enough that at least some cells in the assays of interest can traverse into the holes or pores and potentially migrate through the membrane. Ideally, these holes or pores are large enough for a measurable fraction of the cells to traverse. An example of Cell Transparent Membrane is the membrane manufactured by Millipore Inc, (www.millipore.com/cellbiology/cb3/microporousmembrane). Typically, the membrane may be made of polymer film, e.g. polycarbonate, hydrophilic PTFE, mixed cellulose, containing pores or holes of defined range of dimensions. Ideally, the size of the holes in the membranes may be in the range from approximately 1 µm to 20 µm in diameter. For certain cell types, it will be understood that membranes containing holes of other dimensions could also be used.

The membrane thickness is generally in the range from approximately 1 µm up to 1 mm, but more commonly is in the range from approximately 10 µm to 300 µm. The Cell Transparent Membrane is usually not hydraulically tight, meaning that it cannot sustain a significant pressure difference between the two surfaces of the membrane in a liquid-tight manner.

The term "seeded cells" covers cells which are grown on the semi-permeable membrane. These seeded cells may form a confluent or non-confluent layer. Ideally, endothelial cells may be used as the seeded cells.

It will be understood that the semi-permeable membrane may be coated with a substance which alters the seeded cell function or promotes adhesion of the seeded cells to the semi-permeable membrane prior to growth of the seeded cells. These substances may include cell adhesion substances and/or cell transmigration substances.

The term "reagent" or "reagent liquid"/"reagent gel" covers many different types of analyte. The term "analyte" and "reagent" may be used interchangeably in the specification. The reagent may be a chemoattractant, a toxic substance and/or a pharmaceutical preparation. For example, the reagent could be any liquid or gel from a drug under assessment, a poison, a cell nutrient, a liquid or gel containing other cells in suspension, reagent eluting cells or indeed any reagent whose effect on the sample cells requires assessment. It may also cover any reagent which activates a defined cell function, such as a cell adhesion molecule or cell transmigration molecule. In some embodiments of the invention, the reagent may also be introduced into the sample cell channel. The reagent gel may be in the form of a solid or semi-solid gel. For example, the reagent liquid may comprise ECM gel containing IL-8. It will also be understood that the reagent in certain cases may be a placebo.

The term "cell function" means the biological or physiological function of the cells such as cell mobility, cell attachment, cell detachment, cell apoptosis, metabolism, cell death due to the toxic effect of the environment, release of ligands, release of agents involved in cell signaling, cell transmigration, adsorption of the chemicals and ligands from the environment, change in the cell shape, cell rolling and other broadly similar functions.

The term "cell adhesion molecule" means any molecule which facilitates cell adhesion. These include among others members of the immunoglobulin superfamily (such as VCAM-1, ICAM-1, PECAM-1), selectins (such as E-selectin, P-selectin, L-selectin), catherins (such as E-catherin, N-catherin, P-catherin), integrins and any other molecule which will facilitate adhesion of cells in the assay to the walls of the device or the membrane. This also includes components of the extracellular matrix such as collagen, fibronectin, laminin. Any other suitable "cell adhesion molecules" may also be contemplated.

The term "cell transmigration molecule" means any molecule that will activate and facilitate the transmigration of the cells in the assay. This includes chemokines (CC chemokines-such as RANTES/CCL5, MCP-1/CCL2, CCL28; CXC chemokines-such as CXCL12; C chemokines-such as XCL1; CX3C chemokines-such as fractalkine/CX3CL1) and any natural or synthetic molecule that induces a cell to migrate. Any other suitable "cell transmigration molecules" may also be contemplated.

It will also be understood that the walls (i.e. the internal bore) of the channels, in their entirety or part thereof, may be coated with substances which interact with the sample cells.

These substances may include, but are not limited to enzymes, proteins, polysaccharides, glycoproteins, both natural and synthetic collagen. This may also include cell adhesion molecules and/or cell transmigration molecules. To facilitate the attachment of these substances to the walls of the fluidic channel it may be treated, e.g. by plasma treatment, so that they become hydrophilic. This type of treatment will be well known to those skilled in the art.

The term "fluidic channel" or "elongate channel" covers a channel wherein the length of the channel is greater than the width/depth of the channel. Ideally, such a channel has a width in the range from approximately 0.005 to 20 mm, more preferably in the range from approximately 0.1 to 10 mm and a depth in the range of from approximately 0.005 to 3 mm, more preferably in the range from 0.05 to 0.5 mm. It will be understood that the width and the depth of the channel do not need to be constant all across its entire length, and indeed may change considerably between different parts of the channel.

The channel is typically made in polymer material but indeed could also be made in glass or silicon or some other materials either optically transparent or non-transparent.

Furthermore, for ease of manufacturing the cross-section (internal bore) of the elongate channel is ideally non-cylindrical. In most embodiments of this invention we will consider fluidic channels of rectangular cross-section. These are just convenient examples of fluidic channel cross-section that are easy to fabricate and more easy to describe and are by no means limiting. The fluidic channel cross-section could be of any other shape, e.g. near rectangle with rounded corners, oval or semicircle, etc. Ideally, the channel has a non-cylindrical cross-section. Furthermore, the cross-sectional area of the channel may vary along its length.

Ideally, the channel of the invention has an internal bore of approximately 1 to 1000 micron in width, preferably 100 to 500 micron in width. Optionally, the bore of the channel may be substantially identical to capillaries (e.g. of the order 8 microns), venules (e.g. of the order of 20 microns) or post capillary venules of a human or other animals for example.

It will be understood that the channel may be a "microfluidic channel" or "microchannel". such as an "elongate enclosed microchannel". Optionally, the internal bore of the microchannel, is substantially the same size as the post capillary venules or capillaries of an animal, or more particularly, a human. However, this is by no means limiting. It will be understood that post capillary venules have an internal bore of below 50 micron in width.

As it will be readily appreciated by those skilled in the art, typically all the walls of a channel are liquid-tight. For example in the case of a rectangular channel, the channel is comprised of four walls, all of which are not transparent/ permeable to the liquid transported by it. In contrast, in our invention the fluidic channel may be defined in a broader way, wherein in some embodiments one or more walls of the fluidic channel can comprise a Cell Transparent Membrane and therefore, the channel is not necessarily liquid-tight. The channel does not need to be uniform along its entire length. For example, only a fraction of the length of the channel may comprise one wall comprising Cell Transparent Membrane, while for the rest of the channel's length all of its walls may be entirely liquid-tight. Furthermore, the channel may contain membranes of several types. For example, one segment of the channel may contain wall of membrane A and another segment of its length may contain wall of membrane B having different properties.

The term "flow inducing means" encompasses devices which have the ability to induce flow. Generally this means devices capable of supplying the pressure difference across fluidic channel. This may be accomplished by means of syringes, various types of pumps, including the pump as described in the U.S. Pat. No. 6,805,841 (Shvets) which is incorporated herein by reference. The flow can also be induced by means of electrophoretic or osmotic pumping. In preferred embodiment the pressure is induced by means of syringe pump or proprietary Mirus Nanopump® supplied by Cellix Ltd (www.cellixltd.com).

The term "fluidic device" or "biochip assembly" means a device comprising one or more channels or microchannels as defined above being either mutually coupled to each other or decoupled, one or more sample wells, one or more input ports and/or one of more output ports and/or the coupling means such as tubing for coupling liquids in and out from the channels.

In the context of the present invention generally, the fluidic device is used for carrying out biological, medical, chemical, biochemical, biotechnology or drug discovery experiments or tests. The fluidic device may have one or more wells, sealed or unsealed integrated with the device that may be coupled into the channel(s) or decoupled from it (them). The fluidic device may be substantially planar, that is built in into a substantially flat substrate or non-planar. The fluidic device may operate with external pumping means such as pump, syringe, pressure source, electroosmotic pump. The fluidic device may have one or more sensors integrated into it. The device may be connected to the external or internal pumping means by means of rigid or flexible tubing or any other suitable connection means. The channels may be transparent to light or opaque. They can be made of polymer material (e.g. PMMA, polystyrene, polycarbonate etc.), crystalline material (e.g. Si), amorphous material (e.g. glass) or a combination of several material types.

It will be understood that the term "transmigration" does not necessarily imply that the sample cells must migrate all the way across the membrane from the sample cell containing channel to the reagent channel. The transmigration of sample cells across the membrane is one of the most common assays that can be carried out using the device. However, numerous other assays are also possible, including but not limited to:

seeding the sample cells on the membrane, subjecting the sample cells immobilized on the membrane to various chemical agents injected either into the sample channel or the analyte channel, observation of the response of the sample cells immobilized on the membrane to the toxic agents injected at a known concentration, observation of the detachment of the immobilized sample cells from the membrane back into the sample channel, measurement of the shear force causing the detachment of the immobilized sample cells from the membrane, forming the layer of seeded cells on the membrane and observation of interaction of the sample cells with the seeded cells;

migration of the sample cell through the layer of endothelial cell grown on the membrane;

observation of the detachment of the sample cells from the cells seeded on the membrane;

observation of the attachment of the sample cells to the cells seeded on the membrane.

Thus, the assay and method of the invention may be used in the study of cell receptor-ligand interactions and cell-cell adhesion followed by cell migration.

Referring to the drawings, one embodiment of the transmigration device of the invention 1 is shown in FIG. 1. The device 1 comprises a sample channel 3 and an analyte channel 6. In this figure, the sample channel 3 and the analyte channel 6 are in-line and ideally run parallel. In the embodiment shown in FIG. 1 each of the two channels has one input (2,5) and one output (4,7). One could devise embodiments having more than one input and/or one output. The two channels are separated by a semi-permeable membrane 8, ideally a cell transparent membrane, such as e.g. polycarbonate membrane with pore size of 3, 5 or 8 um supplied by Millipore or Nucleopore. In the overlap region 15 the two channels are separated merely by a membrane 8. In the embodiment shown in FIG. 1 the overlap region extends for most of length of the channels. One could also devise an embodiment in which the overlap region covers only a small segment of the channel's length.

It will be understood that the semi-permeable membrane 8 may permit the passage of cells though it and as such may be a cell transparent membrane. Passage of such cells may be unidirectional or bidirectional.

It will be understood that the channel is subjected to continuous flow (for example to mimic the flow of living cells in-vivo). Ideally, both channels are subjected to continuous flow in the same direction or in opposite directions. This assumes that both channels contain sample cells and reagent (analyte) in the form of liquid. If the reagent is in the form of a gel, the analyte channel may be static.

Figure 2:
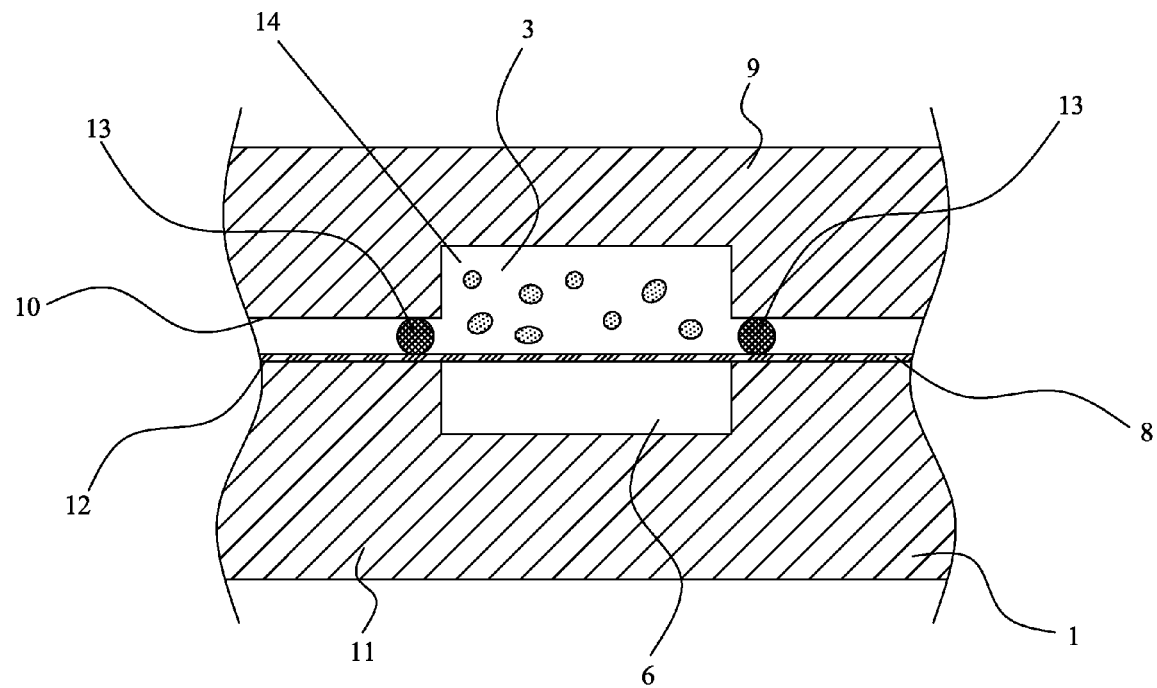
FIG. 2. is a side sectional view of the assembly along the lines A-A' of FIG. 1 showing the semi-permeable membrane separating the sample channel from the analyte channel.

FIG. 2 shows the cross-section A-A' of the two channels of the transmigration device 1 of FIG. 1. Effectively the cell transparent membrane 8 serves as the section of the common wall of the two channels. The widths of the two channels (the sample channel and the analyte channel) and their depths can be identical or different. In some embodiments the channels are elongate enclosed microchannels. FIG. 2 shows the two channels having the same width but this represents only one particular example of the transmigration device embodiment. Thus, the channels separated by a semi-permeable membrane may have different widths.

Figure 14:
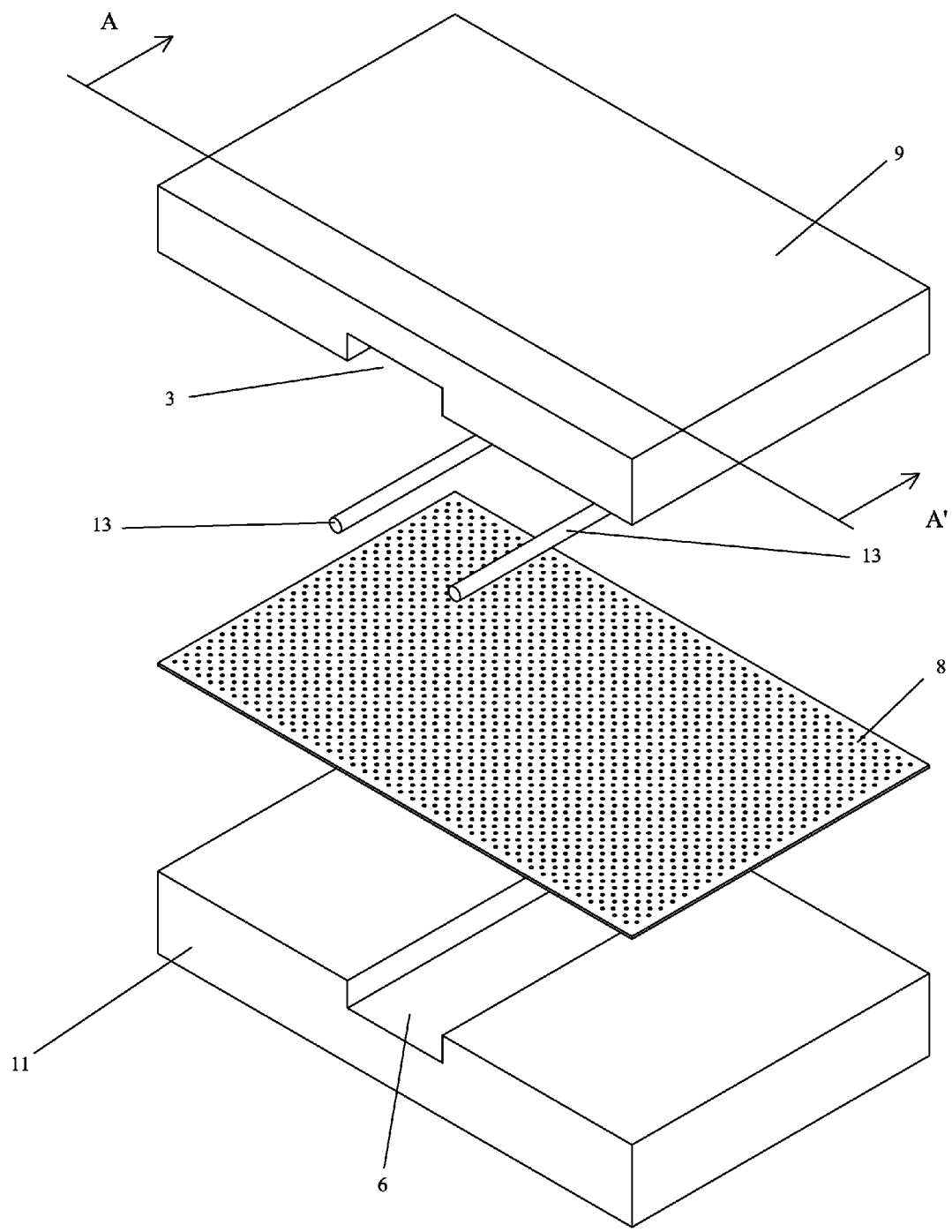
FIG. 14 is an exploded perspective view of the construction of the transmigration device showing the sample channel in line with the analyte channel and where both channels are separated by a semi-permeable membrane.

In one embodiment, the sample channel 3 and the analyte channel 6 can be made by imprinting of a flat plastic substrate (e.g. ABS plastic, PEEK, PET, PMMA, polycarbonate, polypropylene etc) by means such as hot embossing, injection molding or lithographic pattern transfer technique. Ideally, the membrane 8 is in the form of a sheet and is positioned between two substrates, the sample substrate 9 and the analyte substrate 11 which contain the sample channel 3 and the analyte channel 6 respectively. In order to ensure a liquid tight connection, a compression gasket 13 of compressible polymer can be inserted in between the inner surfaces of the two substrates (10, 12). FIG. 14 shows how this particular construction may be assembled in practice.

Figure 15:
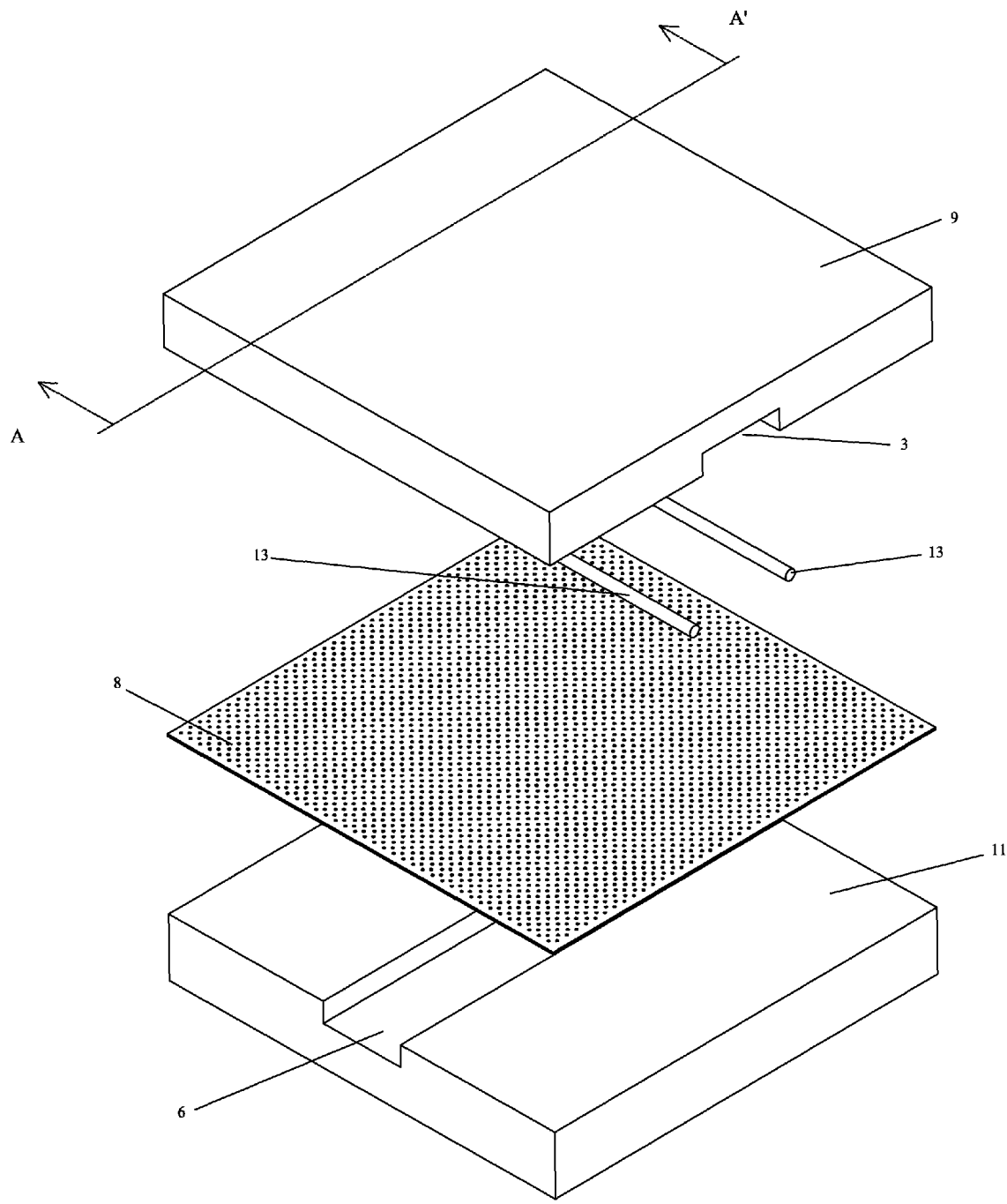
FIG. 15 is an exploded perspective view of the construction of the transmigration device through the intersection of the channels showing the sample channel crossing the analyte channel at one section comprising a semi-permeable membrane.

It will be understood that the two channels, the sample channel 3 and the analyte channel 6, do not have to be in-line or parallel to each other, as shown in FIGS. 1, 2, 11 and 12. This is shown schematically in the embodiment of the transmigration device shown in FIG. 3. They can overlap, intersect or cross along an area (the overlap region) that is small by comparison with the overall area of the channel. FIG. 15 shows how this particular construction may be assembled in practice.

Figure 4:
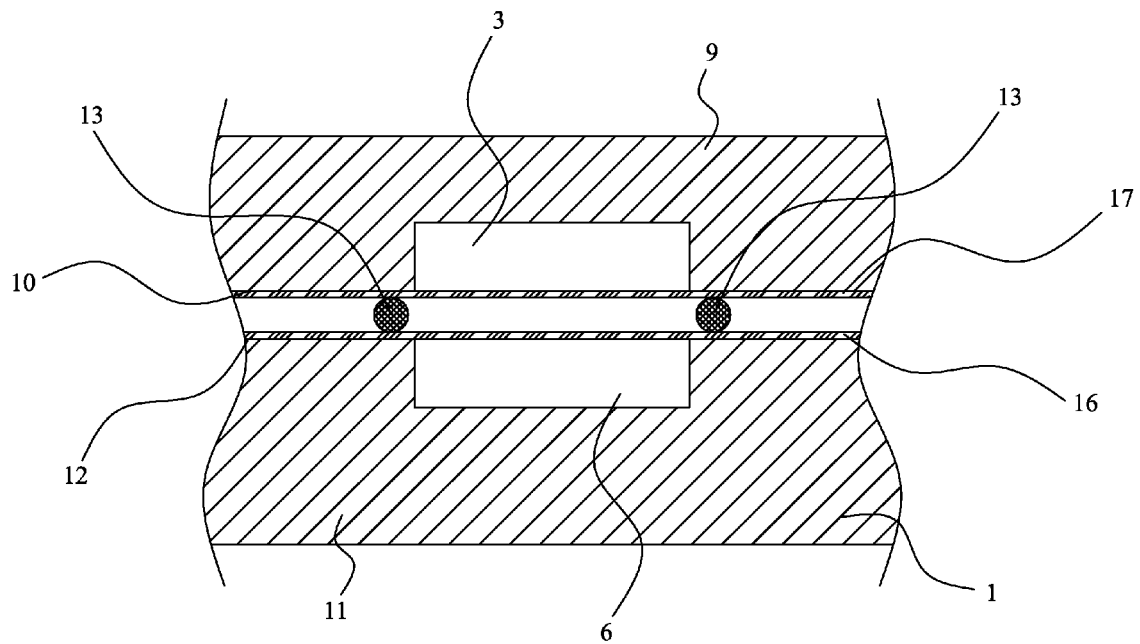
FIG. 4. is a side sectional view of the assembly along the lines A-A' of FIG. 1 showing two separate semi-permeable membranes and a single compression gasket separating the sample channel from the analyte channel.
Figure 5:
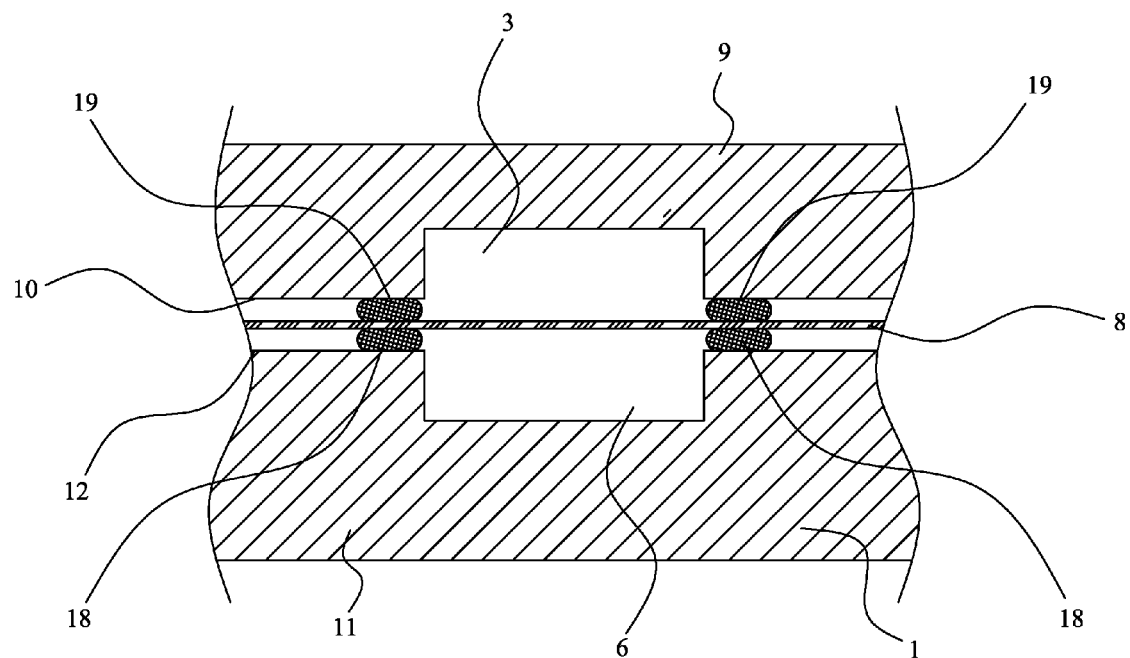
FIG. 5. is a side sectional view of the assembly along the lines A-A' of FIG. 1 showing a semi-permeable membrane separating the sample channel from the analyte channel with two compression gaskets.

Other embodiments of the invention can be contemplated, including, embodiments having more than one membrane 8 or more than one compression gasket 13. For example, FIG. 4 shows an arrangement having two membranes, 16 and 17 and one compression gasket 13. In this case the analyte could be positioned in between the two membranes or alternatively two different types of cells could be seeded on the membranes 16 and 17. Alternatively, the membranes 16 and 17 could be covered by two different types of enzymes. Still alternatively, the membranes 16 and 17 could be membranes of different properties for example different thickness or different extent of transparency to the transmigrating cells. These advantages of the embodiment comprising two membranes are given here by way of example only. Many other configurations of experiments are possible. FIG. 5 shows embodiment of the transmigration device with one membrane 8 and two compression gaskets 18 and 19. The advantage of this embodiment could be that in some cases this transmigration device could be easier manufactured as per embodiment utilizing two compression gaskets and one membrane.

Many other embodiments could be readily devised by those skilled in the art, some are expanded on below as non-limiting examples of the invention.

Figure 6:
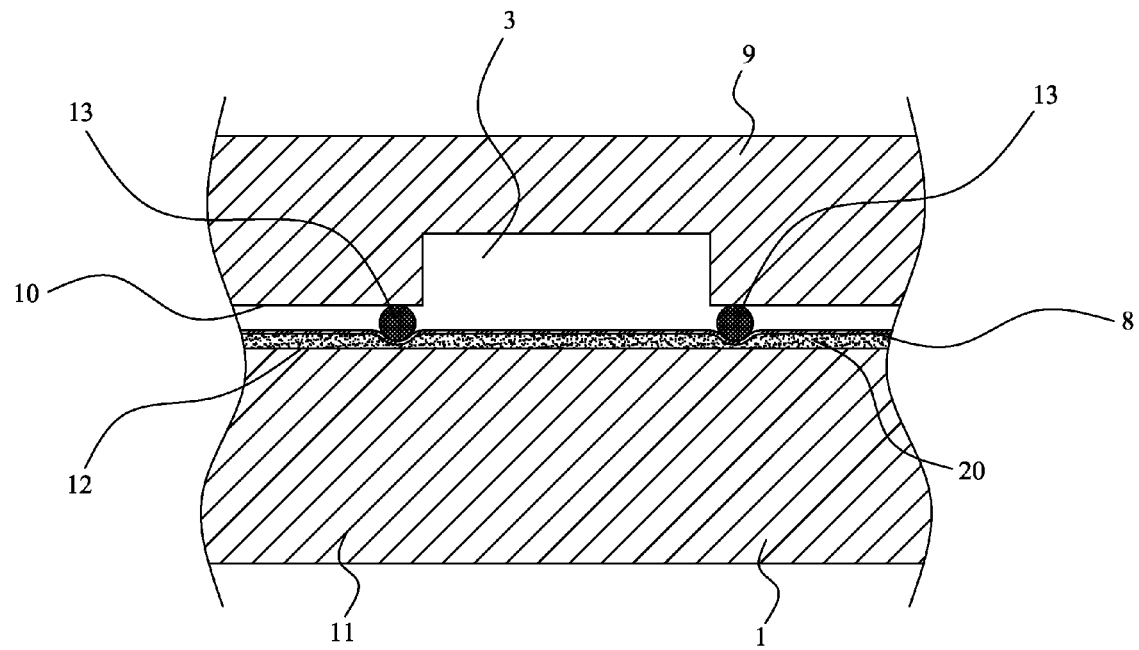
FIG. 6. is a side sectional view of the assembly along the lines A-A' of FIG. 1 showing the semi-permeable membrane separating the sample channel from the analyte channel. In this embodiment one of the channels depth is zero and the semi-permeable membrane abuts one of the channels, preferably the analyte channel. The analyte channel shown is coated with an ECM gel.

For example, in some embodiments the membrane could be laid against the flat inner surface of the substrate (e.g. sample substrate or analyte substrate) and in others it could be bonded to that surface e.g. by means of adhesive or ultrasonic welding. FIG. 6 shows an embodiment of the transmigration device in which the depth of the analyte channel is zero. In this embodiment the semi-permeable membrane 8 abuts either one of the channels. In this embodiment the analyte substrate is a flat substrate. The analyte substrate may be provided with a gel containing, for example, a cell transmigration reagent such as ECM gel 20. Thus, a layer of gel may be sandwiched between the semi-permeable membrane and the analyte substrate.

With reference to FIG. 1, the sample channel input 2 and/or the analyte channel input 5 may be connected to a pumping means to provide cell flow and shear stress. In addition, the sample channel output 4 and/or the analyte channel output 7 may be connected to the collection means such as set of wells or collection reservoir. These are not shown in FIG. 1 for brevity but will be well known to those skilled in this field and are described in the following U.S. Pat. Nos. 6,770,434, 6,805,841 and 7,122,301 and U.S. patent application Ser. No. 10/500,277 by the same inventors the contents of which are herein incorporated by reference.

The following describes one example of the operation of the device. The width of both, the sample channel 3 and the analyte channel 6 is ideally approximately 400 μm and the channel depth is ideally approximately 100 μm. The analyte channel is filled with an ECM gel containing approximately 1-10 nM of IL-8 at the temperature of approximately 4 degrees C. The gel in the analyte channel is allowed to solidify at the temperature of 37 degrees C. for 30 minutes. Primary neutrophil cells were isolated from the whole blood according to the protocol known to those skilled in the field. The neutrophil cells were re-suspended in a culture medium, for example RPMI1640 (Gibco) at the concentration of 5 million/ml and injected into the sample channel and flow at the average linear velocity of 0.83 mm/sec corresponding to the shear stress in the range of 0.5 dyne/cm$^2$. The sample cells 14 are schematically shown in FIG. 2. The flow/continuous flow can be supported by means of a suitable pump such as e.g. Mirus Nanopump™ from Cellix Ltd. The duration of the experiment may be in the range of 20 minutes to 2 hours, although other durations may of course be contemplated. For the duration of the assay, transmigrating and resting neutrophil cells are supplied with a culture medium (necessary to ensure cell viability and survival) through the sample channel 3. The cells migrating through the membrane are ideally observed by means of optical microscope and the number of cells migrating through the membrane is monitored by means of automatic image recognition software such as DucoCell™ analysis software supplied by Cellix Ltd. The results of the experiment can then be compared with reference results obtained under similar conditions, i.e. with the difference being that the ECM gel in the analyte channel does not contain IL-8.

Although, it is contemplated that a first channel of the device contains the sample cells (the "sample channel") and a second channel comprises the reagent (the "analyte channel"), the channels may also comprise additional substances depending on the type of assay being carried out. For example, in order to ensure the sample cells are viable, it may be necessary to introduce a cell culture medium to the channel. Alternatively, liquid media may be needed to supply the cells with oxygen. Furthermore, it may be necessary to stain one or both of the channels. Additionally, the reagent may be introduced into the channel mixed with a gel. Such gels may initially be in the form of a liquid that turns into a gel as the temperature changes. Still additionally, one may want to test a drug candidate to assess changes to transmigration through the membrane caused by a chemoattractant.

In a preferred embodiment of the invention, sample cells are introduced into one channel (e.g. first/sample channel) and a chemical agent that effects their migration is introduced into a second channel (e.g. analyte channel). Such a chemical agent may be in the form of a gel, so that the second channel/analyte channel is static. Optionally, the semi-permeable membrane may have a layer of cells seeded on it, enabling the study transmigration of cells through the seeded cell layer.

In an alternative embodiment of the invention, sample cells A may be introduced into a first channel and reagent eluting sample cells B may be introduced into a second channel. Each channel may also contain cell growth media. 2. Sample cells B may then release a reagent that causes cells A to migrate from the first channel to the second channel. It will be understood that many other configurations will be possible.

Figure 7:
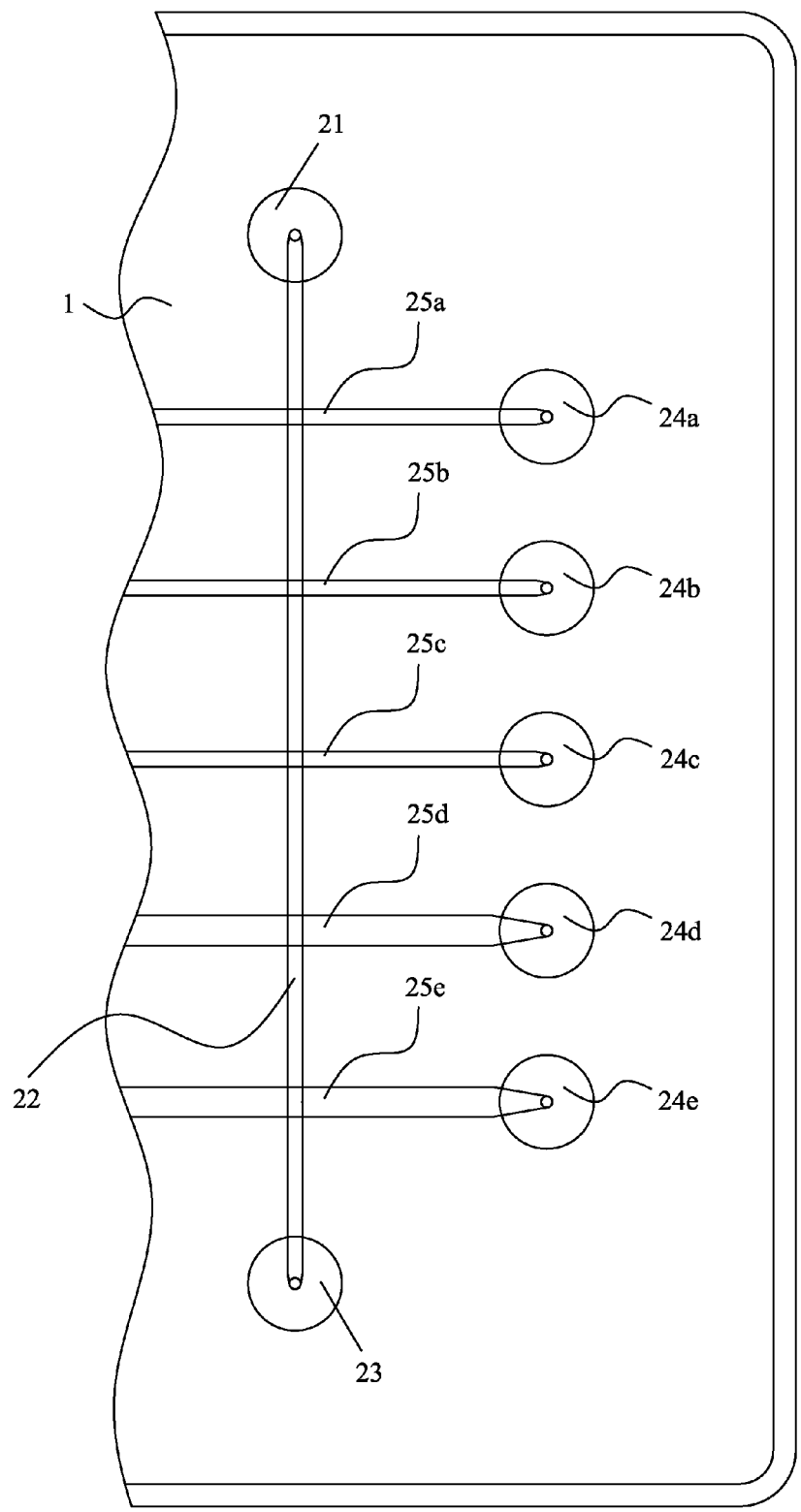
FIG. 7. is a plan view of a transmigration device of the invention showing multiple sample channels intersected by a single analyte channel.
Figure 8:
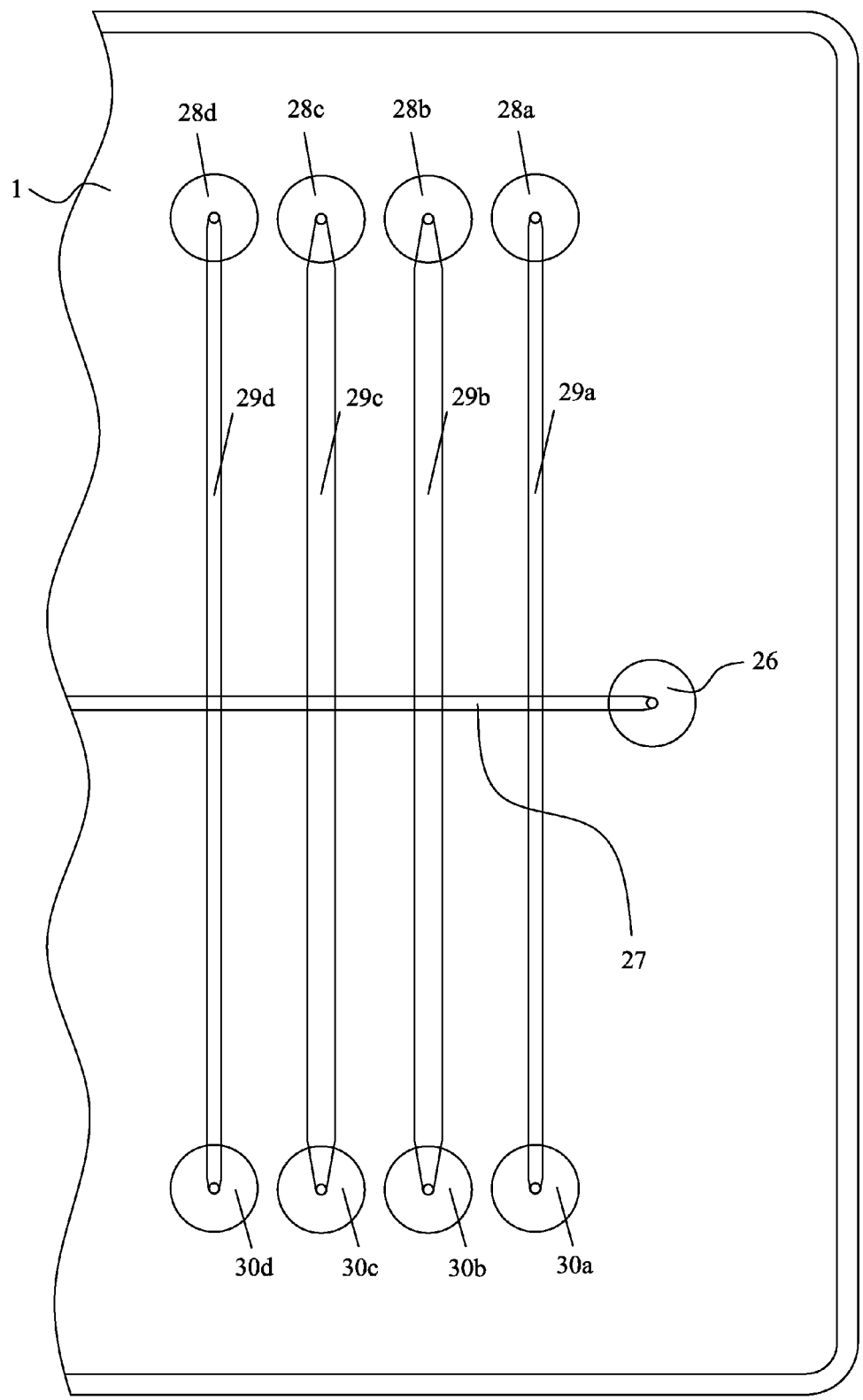
FIG. 8. is a plan view of a transmigration device of the invention showing a single sample channel intersecting multiple analyte channels.
Figure 9:
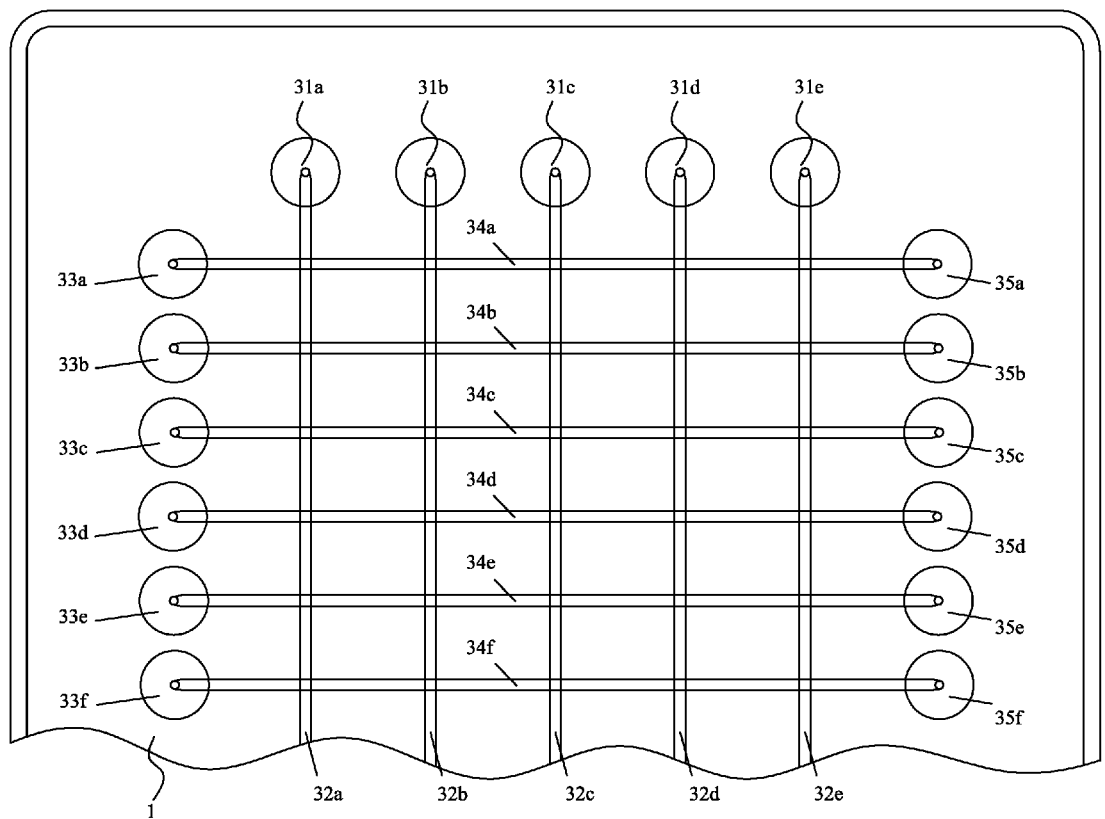
FIG. 9. is a plan view of a transmigration device of the invention showing multiple sample channels intersecting multiple analyte channels. Any number of channels may be used and the number of analyte channels and sample channels may be the same or different.

Further embodiments of the transmigration device are shown in FIGS. 7, 8 and 9. These embodiments comprise multiple intersections of sample and analyte channels. For example, FIG. 7 shows the embodiment where one analyte channel 22 (analyte channel input 21 and analyte channel output 23) crosses a number of sample channels 25a to 25e (sample channel input 24a to 24e). The locations of intersections of the analyte channel 22 with the sample channels 25a to 25e include membranes as described with reference to FIGS. 1 to 6. The membranes are not shown in FIG. 7. It will be understood that the widths of all the sample channels do not have to be identical. The sample channels can transport different cell types ($C_1, C_2, \ldots, C_n$) and in this way the transmigration function could be tested in a variety of cell lines at the same time against the same cell transmigration molecule. The sample channel outputs are not shown in FIG. 7.

Likewise the same sample channel 27 (sample channel input 26) could intersect a number of analyte channels 29a to 29d (analyte channel input 28a to 28d, analyte channel output 30a to 30d) and this embodiment is shown in FIG. 8. In this way the same cell type could be tested against the variety of cell transmigration molecules. The sample channel output is not shown in FIG. 8.

For example, consider FIG. 8, with the liquid in the sample channel 27 moving downwards. Then there is increasing concentration of the same chemical in the analyte channels subsequent 1,2,3,4 marked with numerals 29a, 29b, 29c, 29d, respectively, e.g. analyte channel 1 (29a) has concentration x, channel 2 (29b): 5x, channel 3 (29c): 25x, channel 4 (29d): 125x. Then the contamination from the analyte channel 1 (29a) should be negligible as at the point of the analyte channel 2 (29b) intersection with the sample channel, the concentration of the same analyte is much higher anyway. Likewise the concentration of the analyte from the analyte channel 2 (29b) at the cross section of analyte channel 3 (29c) with the sample channel is also much smaller than the concentration of the analyte directly from the analyte channel 3 (29c), etc. In this manner cross-contamination is not an issue. In addition, if the reagent in the analyte channel is in the form of a gel, cross-contamination is not an issue as the gel would not be expected to elute much reagent into the sample channel.

In addition, another embodiment may comprise the intersection of a variety of sample channels 32a to 32e and analyte channels 34a to 34f in one transmigration device 1 as schematically shown in FIG. 9. In this way the variety of cells could be simultaneously tested against the variety of cell transmigration molecules. The sample channels outputs are not shown in FIG. 9. Sample channel inputs 31a to 31e are shown along with analyte channel inputs 33a to 33f and analyte channel outputs 35a to 35f.

Figure 10:
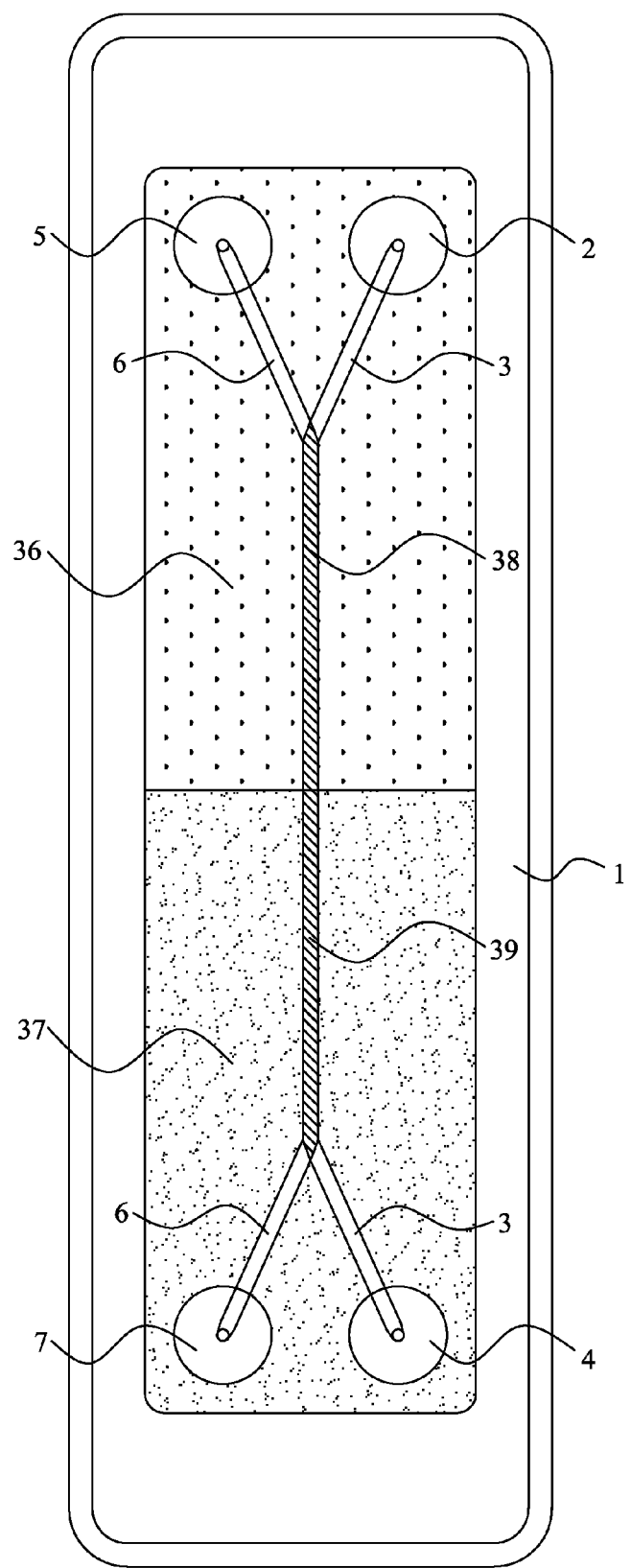
FIG. 10. is a plan view of a transmigration device of the invention showing the sample channel and analyte channel in line and two semi-permeable membrane types.

FIG. 10 shows an embodiment of the transmigration device whereby the cell transparent membrane has several regions 36 and 37 each one being characterized by a different set of membrane properties. For example, the membrane could comprise two areas each one being characterized by a different pore size. Alternatively, it could be comprised of two areas having the same pore sizes but different membrane thickness. These regions are schematically marked in FIG. 10 as overlap region 1 (38) and overlap region 2 (39). It will be understood that a single cell transparent membrane may have different membrane properties or when multiple membranes are used, each separate membrane may have different properties. If multiple membranes are used, they may form a continuous membrane area or a non-continuous membrane area.

Figure 11:
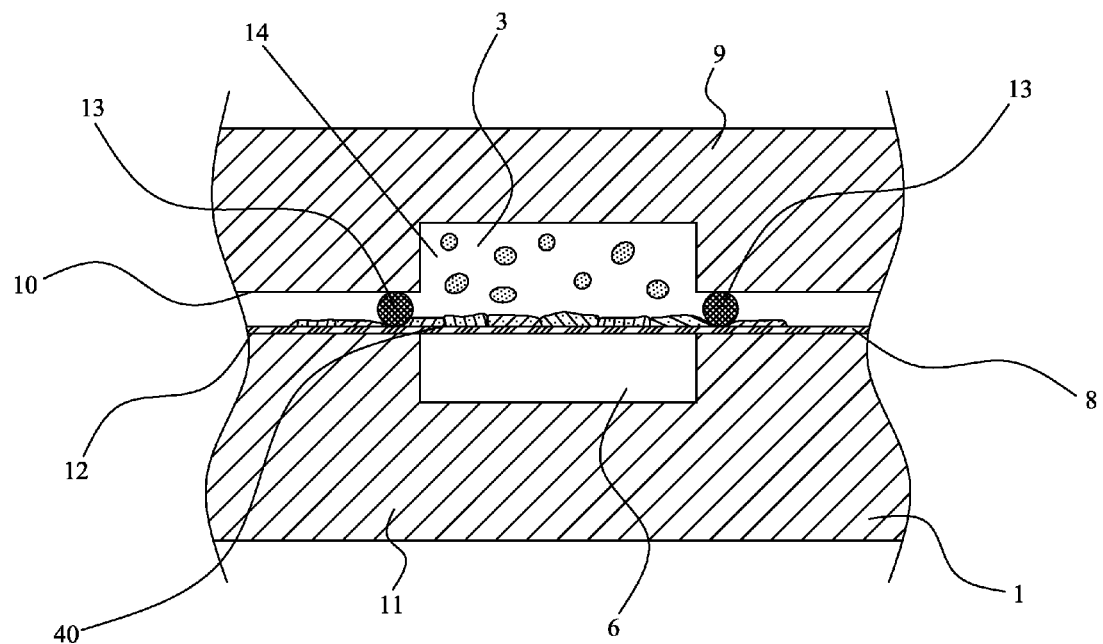
FIG. 11. is a side sectional view of the assembly along the lines A-A' of FIG. 1 showing the semi-permeable membrane separating the sample channel from the analyte channel. In this figure cells are seeded on the semi-permeable membrane.

FIG. 11 shows another embodiment of the transmigration device where a layer of cells 40 is allowed to form on the membrane. The layer of cells could be e.g. a confluent layer of endothelial cells. However, other cells could also be seeded on the membrane. Thus, in one embodiment, the layer is a confluent layer of cells. Alternatively, the layer of cells are non-confluent i.e. bare areas could be left on the membrane 8.

To seed the cells on the membrane 8, the membrane could be covered by specific adhesion molecules such as fibronectin (Sigma Inc). More preferably the layer of cells is grown on the membrane when it is removed from the transmigration device and placed into the cell culture incubator at 37° C., 5% $CO_2$ and 80% humidity. Typically endothelial cells are seeded at the density of approximately 75000/cm$^2$ and allowed to grow for a period of 48 hours until a confluent layer of endothelial cell is formed. Different primary endothelial cells and cell lines may require different density and seeding time. Following seeding, the membrane with seeded cells 40 is placed between the sample and the analyte channels 3 and 6 and sealed by way of compression gasket 13. Subsequently, sample cells 14 are injected into the sample channel 3 and the interaction between the sample cells 14 and the seeded cells 40 is observed. This interaction could include by way of example the migration of the sample cells through the layer of seeded cells, migration of the sample cells through the layer of seeded cells and thought the membrane, adhesion of the sample cells to the seeded cells.

Figure 12:
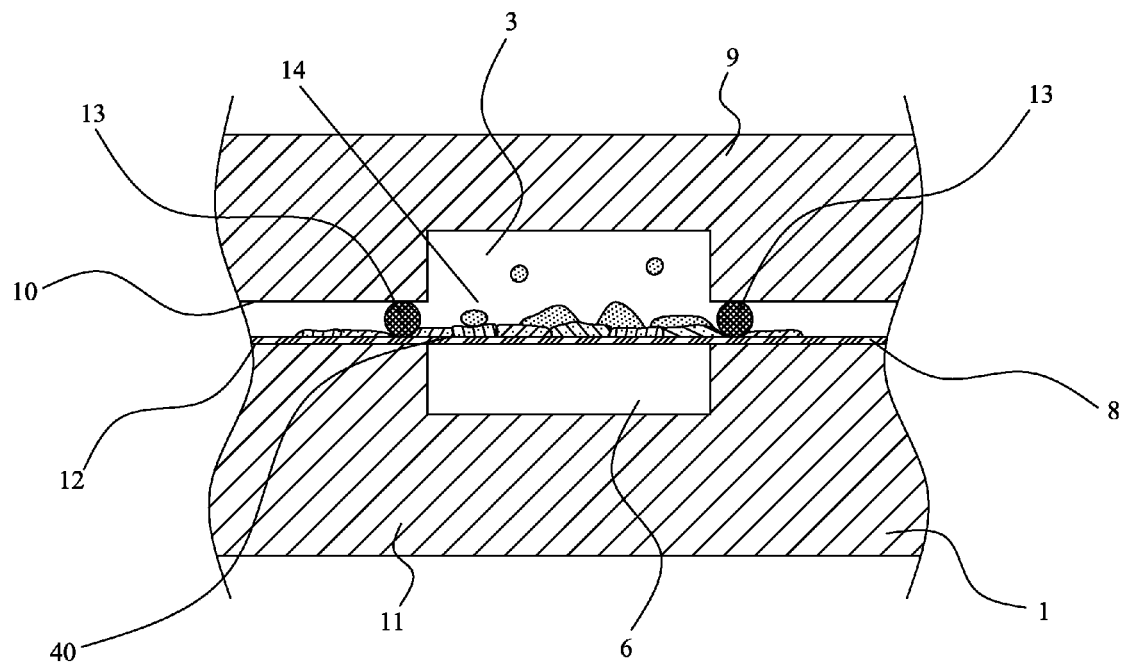
FIG. 12. is a side sectional view of the assembly along the lines A-A' of FIG. 1 showing the semi-permeable membrane separating the sample channel from the analyte channel. In this figure a further layer of cells has seeded itself on the cells previously seeded on the semi-permeable membrane.

In a further embodiment, the layer of the sample cells 14 could seed on the layer of the seeded cells 40 as shown in FIG. 12. Then the sample cells 14 could be subjected to interaction with various chemicals injected either in the sample channel or the analyte channel. In yet a further embodiment the layer of seeded cells as shown in FIG. 12 could be subjected to the chemical injected either in the sample channel 3 or in the analyte channel 6.

Figure 13:
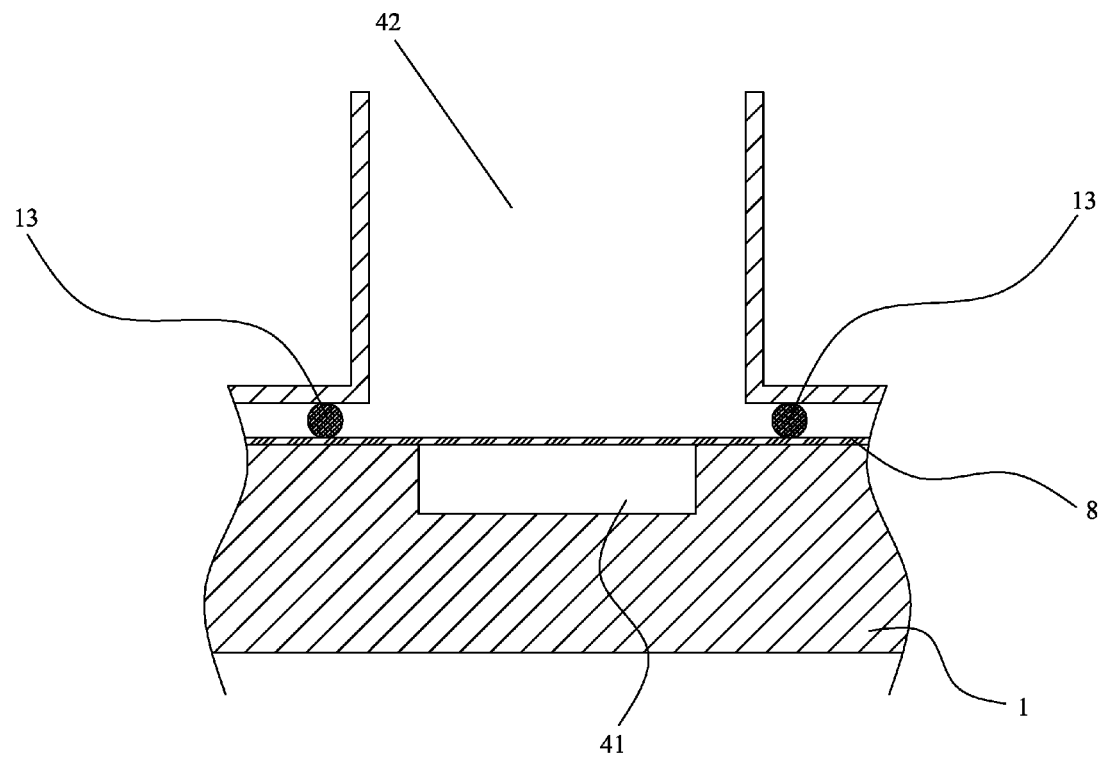
FIG. 13 is side sectional view of an alternative embodiment of the invention showing a single channel separated from a well by a semi-permeable membrane.

FIG. 13 shows an alternative embodiment of the device of the invention in which one of the channels is a well 42. Ideally, the analyte channel is in the form of an open well 42, with no input or output. In this embodiment, transmigration molecules may be in the form of a gel, which is placed in the well 42. The semi-permeable membrane is placed at the bottom of the gel.

Figure 3:
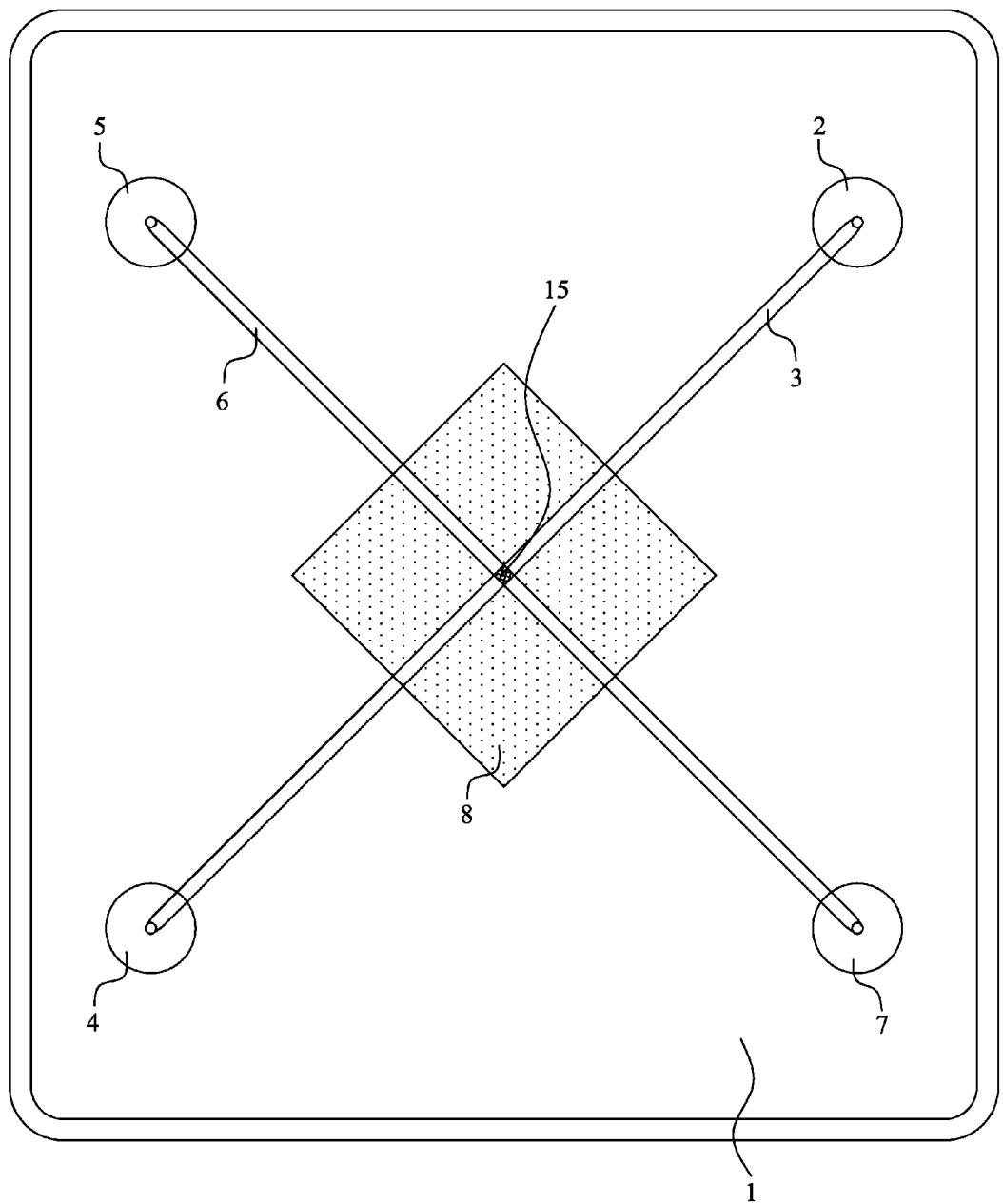
FIG. 3. is a plan view of a transmigration device of the invention showing the sample channel and analyte channel crossing the analyte channel at one section comprising a semi-permeable membrane.

FIGS. 14 and 15 show expanded perspective views of the contraction of the devices of FIG. 1 and FIG. 3 respectively. These figures show how the biochips 1 are made of sheets of plastic materials bonded together. Again, parts similar to those described, with reference to the previous drawings, are identified by the same reference numerals. FIG. 14 shows the channels (non-cylindrical bore) 3 and 6 formed in plastics material surrounding a sheet of membrane 8. The channels are in-line. FIG. 15 shows the channels 3 and 6 separated by the sheet of membrane 8 crossing at a single intersection location.

Cells flowing through the channels may be observed via a microscope and images may be captured and analysed at a later date. For this one could use conventional microscope or alternatively, a more specialist microscope, such as confocal or fluorescent microscope or indeed any other microscope known in the field of cell imaging and analysis.

Various different imaging technologies can be used in conjunction with the invention. Furthermore, various different image processing programmes for analysis and processing of the acquired images can also be used in conjunction with the invention. Finally, one could use positive displacement or pressure driven pump to move cells and analyte in the channels.

Some examples of these technologies and software follow.

For example, Cellix Ltd. has developed a novel Microfluidic Platform consisting of a PC-controlled Nanopump® with microfluidic biochips (such as Vena8® biochips (Cellix Ltd.) previously developed or the elongate enclosed channels of the invention) and DucoCell® (Cellix Limited) analysis software. The Nanopump® enables very accurate flow rates to be achieved which are more reproducible and consistent compared to anything currently available. Importantly, flow rates are extremely low (5 pL min-1 to 10 μL min-1) and the shear stress levels that the pump can mimic (up to 30 dyne cm-2) are equivalent to those found in blood vessels in vivo. The Nanopump® is vital to the use of small diameter capillaries as standard syringe pumps are incapable of delivering the required low flow rates.

In order to carry out an assay using the above platforms, the following general protocol may be used:

First of all, the cell type to be analysed must be determined, followed by establishing how to harvest such cells e.g. culturing in growth media, or isolation from in vivo fluids.

Secondly, the assay itself should be outlined, including whether live cells or proteins will be coating the channels of the biochip. If it is the former, protocols for culturing the cells both outside and inside the biochip channel must be established. Thirdly, the adhesion profile of the cells to be passed through the coated channel should be determined.

Next, if exogenous compounds are being analysed, these should then be introduced to the system and their effect on the adhesion profile assessed. This should include calculation of required concentrations and pre-incubation conditions, before introduction to the system. Finally, the images taken via the digital camera attached to the microscope should be masked and analysed using the Ducocell® software.

Various specific assays may be contemplated using these platforms including but not limited to:

A microfluidic assay assessing the effect of levocetirizine on human eosinophil adhesion, involving the following The method involves coating each microcapillary for one hour in humid conditions at ambient temperature with either human vascular cell adhesion molecule-1 (rhVCAM-1) or bovine serum albumin (BSA) (both 10 μg mL-1 in HBSS containing Ca2+ and Mg2+). All capillaries were then coated with BSA to occupy non-specific binding sites. Resting or Granulocyte-macrophage colony-stimulating factor (GM-CSF)—treated eosinophils were pre-incubated at 37° C. in a water bath for 10 mins before incubation with/without levocetirizine (0.1 nM-100 nM), with anti-VLA-4 mAb as a positive control) for a further 20 mins.

Eosinophils were infused into the capillaries (microfluidic biochips) at stepwise increases in shear stress, from 0 to 5 dyne cm-2, one minute per shear stress level. Images at each shear stress level were captured using the accompanying PixeLINK microscopy software. For experiments with GM-CSF-stimulated (1 ng mL-1) eosinophils, the cytokine was added to the warmed cells at the same time as levocetirizine and incubated at 37° C. for 20 mins prior to commencing the flow assay. Adhesion was evaluated by monitoring eosinophil migratory behaviour in real time with images captured via a digital camera connected to the microscope.

Image analysis—several images per shear stress level may be captured and adhered eosinophil numbers can be recorded using Ducocell® application software. Data was exported into Excel for interpretation. Statistical significance was determined by Students unpaired t-test, and P>0.05 was considered statistically significant. Data was presented as mean±s.e.mean.

A microfluidic assay assessing the adhesion profiles of peripheral blood lymphocytes (PBLs).

A microfluidic assay assessing the adhesion profile of platelets on various matrix proteins.

A microfluidic assay assessing novel anti-inflammatory effects of montelukast (MLK) on resting and GM-CSF-stimulated eosinophils using the Cellix VenaFlux® platform to mimic physiological adhesion to rhVCAM-1.

A microfluidic investigation of T-cell adhesion to ICAM-1 with a mixed sepsis model treated with a range of statins under physiological shear stress using the Cellix Microfluidic Platform SP 1.0.

Cell harvesting and sample treatments

Peripheral blood was donated by 6 healthy subjects. Following mononuclear cell isolation, monocytes were allowed to adhere to the culture vessels before B-cells were removed from the T-cell population using nylon wool adhesion.

T-cells were then co-cultured in the presence of monocytes.

Cells were treated with 10 nM meva-, lova- or simvastatin dissolved in ethanol (0.1% v/v final) or prava- or fluvastatin dissolved in water. Cells were then stimulated with 2 μg/ml lipopolysachharide (LPS) and 20 μg/ml peptidoglycan G (PepG). Control cells were treated with 0.1% v/v ethanol±LPS/PepG and incubated a humidified 37° C. incubator containing 5% CO2 for 18 hours.

Biochip coating procedures
  Each microchannel (400 μm wide, 100 μm deep) was coated overnight in humid conditions at 4° C. with rhICAM-1 (10 μg/ml), before being coated with BSA, 10 μg/ml. Two additional channels were coated with BSA for 2 hrs at room temperature. Prior to shear experiments, all channels were washed thrice with media.
Adhesion profiles
  Isolated T cells were infused into the rhICAM-1 and BSA coated channels under a defined shear stress of 0.5 dyne cm-2 for a time period of 5 minutes in $CO_2$ independent media.
  Images were captured using the accompanying PixelLink imaging software.
Image analysis
  T cell adhesion profiles of single cells were recorded using DucoCell® software. Cell images were captured from three microscopic fields from each channel. Data was exported into Excel to allow further analysis.
Statistics
  Data obtained from this experiment can be analyzed using the Wilcoxon's signed-rank test using Graphpad Prism® 4 software.
A microfluidic assay to elucidate the importance of physiological shear stress environment required for *E. coli* adhesion, colonisation and biofilm formation using the Cellix VenaFlux® Platform.
  Biochip Coating Procedure:
    Each microchannel (400 μm wide, 100 μm deep) was coated in humid conditions at 37° C. for 45 min with 10 μl of either 200 μg/ml mannose-BSA (monomannase), 20 ug/ml RnaseB (trimannose); or 10% BSA. Prior to flow experiments each channel was washed three times with PBS-0.2% BSA and quenched with PBS-0.2% BSA for 15 min to decrease non-specific binding.
  Adhesion Profiles:
    Bacteria was infused into the 1M, 3M and BSA coated channels using pre-defined shear steps from 0.1, 0.3, 1.0 and 8.0 dyne/$cm^2$, 100 s per shear stress level.
  Image Analysis:
    *E. coli* adhesion profiles of single cells were recorded using MetaMorph software. Cell images were captured from three microscopic fields from each channel and further analysed by ImageJ and Cellix's DucoCell® software. Data was exported into Excel to allow further analysis.
A microfluidic assay to examine differential cell adhesion within an isogenic model of melanoma progression under physiological shear flow conditions using the Cellix VenaFlux™ Platform.
A microfluidic assay to screen a range of novel thermoresponsive polymers designed to be used as dual drug-eluting systems in coating stents. Specifically, to assess the ability of xemilofiban released in conjunction with fluvastatin, to prevent thrombus formation/platelet adhesion to fibrinogen using Cellix's VenaFlux® platform.

It will be understood that the device described may be called a transmigration device. As explained above, this term does not imply that the sample cells must migrate all the way across the membrane from the sample channel into the analyte channel. Such a transmigration of sample cells across the membrane is indeed one of the most common assays that can be carried out using the device. However, we also described numerous other assays such as seeding the sample cells on the membrane, subjecting the sample cells immobilized on the membrane to various chemical agents injected either into the sample channel or the analyte channel, observation of the response of the sample cells immobilized on the membrane to the toxic agents injected at a known concentration, observation of the detachment of the immobilized sample cells from the membrane back into the sample channel, measurement of the shear force causing the detachment of the immobilized sample cells from the membrane, forming the layer of seeded cells on the membrane and observation of interaction of the sample cells with the seeded cells; migration of the sample cell through the layer of endothelial cell grown on the membrane; observation of the detachment of the sample cells from the cells seeded on the membrane; observation of the attachment of the sample cells to the cells seeded on the membrane. Thus, the device of the invention may be used to carry out multiple assays on living cells, the transmigration aspect is merely a preferred embodiment of the invention.

In the specification, the terms "comprise, comprises, comprised and comprising" or any variation thereof and the terms "include, includes, included and including" or any variation thereof are considered to be totally interchangeable and they should all be afforded the widest possible interpretation.

The invention is not limited to the embodiment hereinbefore descried, but may be varied in both construction and detail within the scope of the claims.

What is claimed is:

1. A method for measuring the transmigration of cells in an assembly comprising a sample channel and an analyte channel or chamber which are in fluid communication in an overlap region between the sample channel and the analyte channel or chamber, said sample channel being separated from said analyte channel or chamber in said overlap region by a semi-permeable membrane mounted between the sample channel and the analyte channel or chamber, the method including:
  introducing a reagent into the analyte channel or chamber mixed with a gel which is a solid gel or is initially in the form of a liquid that is allowed to solidify in the analyte channel or chamber,
  delivering sample cells in a liquid carrier medium at a controlled flow rate through the sample channel on one side of the semi-permeable membrane whereby said sample cells are separated from the reagent in the analyte channel or chamber by the semi-permeable membrane, and
  measuring the transmigration of sample cells from the sample channel through the semi-permeable membrane into the analyte channel or chamber under the influence of the reagent in the analyte channel or chamber.

2. The method of claim 1 wherein the method takes place in an elongate enclosed channel having a semi-permeable membrane mounted therein.

3. The method of claim 1 wherein the method includes coating at least one side of said semi-permeable membrane with a substance which promotes adhesion of cells to the semi-permeable membrane.

4. The method of claim 3 further comprising forming a layer of seeded cells on at least one side of said semi-permeable membrane.

5. The method of claim 4 wherein said layer of seeded cells is formed and mounted in the channel prior to use.

6. The method of claim 4 wherein the seeded cells comprise endothelial cells and the method includes forming a confluent layer of endothelial cells on said semi-permeable membrane and studying the transmigration of sample cells through the layer of endothelial cells.

7. The method of claim 4 wherein the interaction between said seeded cells and said sample cells is monitored and/or recorded.

8. The method of claim 4 comprising a further step of coating an internal bore of the channel prior to use with a substance which interacts with said seeded and/or sample cells.

9. The method of claim 8 wherein a physiological function of said interacting cells is monitored and/or recorded.

10. The method of claim 4 wherein a physiological function of said seeded cells is measured as a function of the shear stress within the channel.

11. The method of claim 1 or claim 4 wherein cell to cell interactions and cell to analyte interactions are measured.

12. The method of claim 1 wherein said channel is a microchannel.

13. The method of claim 1 further comprising coating at least one side of the semi-permeable membrane with one or more substances which affect cell function prior to forming a layer of seeded cells on said semi-permeable membrane.

14. The method of claim 1 wherein the controlled flow rate of the sample cells is sustained by a pressure driven pumping system or a positive displacement pumping system.

15. The method of claim 1 wherein the method includes filling the analyte channel or chamber with the gel containing the reagent at a temperature of 4° C. and allowing the gel in the analyte channel or chamber to solidify at a temperature of 37° C. for 30 minutes.

16. A method for measuring the transmigration of cells in an assembly comprising a sample channel and an analyte channel or chamber which are in fluid communication in an overlap region between the sample channel and the analyte channel or chamber, said sample channel being separated from said analyte channel or chamber in said overlap region by a semi-permeable membrane mounted between the sample channel and the analyte channel or chamber, the method including:
  introducing a reagent into the analyte channel or chamber mixed with a gel which is a solid gel or is initially in the form of a liquid that is allowed to solidify in the analyte channel or chamber,
  coating at least one side of the semi-permeable membrane with a substance which promotes adhesion of cells to the semi-permeable membrane,
  forming a layer of seeded cells on the semi-permeable membrane,
  delivering sample cells in a liquid carrier medium at a controlled flow rate through the sample channel on one side of the semi-permeable membrane whereby said sample cells are separated from the reagent in the analyte channel or chamber by the semi-permeable membrane, and
  measuring the transmigration of sample cells from the sample channel through the layer of seeded cells under the influence of the reagent in the analyte channel or chamber.

17. The method as claimed in claim 16 wherein the seeded cells comprise endothelial cells.

18. The method of claim 17 wherein the method includes forming a confluent layer of endothelial cells on the semi-permeable membrane.

* * * * *